United States Patent
Daniel

(10) Patent No.: US 6,484,051 B1
(45) Date of Patent: Nov. 19, 2002

(54) COINCIDENT MULTIPLE COMPTON SCATTER NUCLEAR MEDICAL IMAGER

(76) Inventor: James Daniel, 1708 Justin Dr., Gambrills, MD (US) 21054

( * ) Notice: Subject to any disclaimer, the term of this patent is extended or adjusted under 35 U.S.C. 154(b) by 30 days.

(21) Appl. No.: 09/854,467

(22) Filed: May 15, 2001

(51) Int. Cl.[7] .................................................. A61B 6/00
(52) U.S. Cl. ............. 600/436; 250/370.09; 250/370.08; 250/363.03
(58) Field of Search ..................... 600/436; 250/363.03, 250/370.08, 370.09

(56) References Cited

U.S. PATENT DOCUMENTS

| | | | |
|---|---|---|---|
| 4,833,327 A | 5/1989 | Hart | |
| 5,506,408 A | 4/1996 | Vickers et al. | |
| 5,567,944 A | 10/1996 | Rohe et al. | |
| 5,821,541 A | * 10/1998 | Tumer | 250/370.09 |
| 6,420,711 B2 | * 7/2002 | Tumer | 250/370.09 |

OTHER PUBLICATIONS

Z. Liang and R. Jaszczak, *Comparisons of Multiple Photon Coincidence Imaging Techniques*, IEEE Transactions on Nuclear Science, vol. 37, No. 3, Jun. 3, 1990.

Z. Liang, *Preliminary Study of Triple Photon Coincidence Imaging Technique*, SPIE, Vol. 974, Applications of Digital Image Processing XI, 1988.

* cited by examiner

*Primary Examiner*—George Manuel
*Assistant Examiner*—Devaang Shah
(74) *Attorney, Agent, or Firm*—Larson & Taylor, PLC

(57) ABSTRACT

A Compton imager and method are provided for generating three-dimensional images. The Compton imager detects Compton scattering of simultaneously or nearly simultaneously emitted gamma rays produced by a radio-nuclide. A possible location of each radio-nuclide decay is defined by the intersection of Compton direction cones corresponding to the detected gamma rays. Three-dimensional images are generated by superposition of individual locations of separate radioactive decay locations.

59 Claims, 10 Drawing Sheets

COINCIDENT MULTIPLE COMPTON SCATTER NUCLEAR MEDICAL IMAGER

BACKGROUND OF THE INVENTION

1. Field of the Invention

The present invention relates to gamma ray imaging, and in particular, to nuclear medical imaging using Compton scattering of gamma rays simultaneously emitted by a radio-nuclide.

2. Background of the Invention

Nuclear medical imaging is an important research and clinical tool. The two common techniques used are Single Photon Emission Computed Tomography (SPECT) and Positron Emission Tomography (PET). These are extensively used to investigate the function of various organs and to determine the location and morphology of malignant tissue. Both SPECT and PET techniques use radio-nuclides which are administered to a patient. In SPECT a variety of radio-pharmaceuticals are used to study various tissue functions such as heart and kidney function and to locate cancer tissue. An exemplary application of PET imaging includes the use of positron emitting isotopes such as $^{15}O$ and $^{18}F$ to investigate brain function.

In SPECT applications, a radio-pharmaceutical is administered to a patient. Nuclei of the radio-pharmaceutical decay with the emission of gamma rays. The location of the gamma ray emission is imaged using collimated, position-sensitive gamma ray detectors. Each detected gamma ray is assumed to have arrived at the detector through the collimator. A single SPECT detector can provide a two-dimensional image of the distribution of the radio-nuclides. By moving the detector to obtain many views of a region-of-interest from different directions or using several detectors to simultaneously view the region-of-interest from different directions, coupled with the use of computer algorithms, it is possible to reconstruct a three-dimensional structure of the radioactivity.

SPECT is most frequently used with relatively low-energy gamma rays because it is difficult to fabricate collimators that are effective for gamma rays above several hundred keV. A very widely-used radio-nuclide for SPECT is $^{99m}Tc$ which emits a 140 keV gamma ray with a half-life of approximately six hours. Other commonly used radio-nuclides used with SPECT include $^{67}Ga$ (93 keV), $^{111}In$ (172 and 245 keV), $^{131}I$ (364 keV), and $^{201}Tl$ (70–80 keV X-rays).

A major limitation with SPECT is the small field-of-view provided by the collimators and the associated very low fraction of the gamma rays that pass through the collimator to the detector. Typically only 0.001%–0.01% of the gamma rays pass through the collimator to the detector. This results in a trade-off between sensitivity and resolution of SPECT imaging. Coarse collimators transmit a higher percentage of the gamma rays but with a poor image resolution. For example, an average image resolution for many clinical applications is around one cm. Conversely, fine collimators provide improved imaging resolution, e.g. around three to five mm, but with lower sensitivity and/or higher radiation doses to the patient. Because of the low detection efficiency, rather large doses of tens of milli-curies must be administered to the patient to achieve adequate images.

In PET, a positron-emitting radio-nuclide is administered to a patient. Commonly used PET radio-nuclides include $^{11}C(\tau_{1/2}=10\text{ m})$, $^{15}O(\tau_{1/2}=2\text{ m})$, and $^{18}F(\tau_{1/2}=110\text{ m})$. Positrons interact with electrons in the surrounding tissue of the patient and emit two 511 keV gamma rays in opposite directions, at an angle of almost exactly 180 degrees. These gamma rays interact in position-sensitive gamma ray detectors, and restrict the origin of the gamma rays to the line joining the two detection positions. Accumulation of a large number of such events along many differing lines of position enables the reconstruction of a three-dimensional image of the radioactivity. The position resolution in PET is typically three to five mm, and is limited by the position resolution in the detectors and the range of the positrons in the body of the patient.

An advantage of PET over SPECT is that higher efficiency is achieved since collimators are not required. However, a disadvantage of PET is a higher cost of PET systems relative to SPECT systems.

Both SPECT and PET have the disadvantage that for each nuclear decay event detected (i.e., a single gamma ray in SPECT and coincident 511 keV gamma rays in PET), the location of the radio-nuclide is only determined to a line within the region-of-interest. As a result, a large number of events (e.g., thousands to millions) must be recorded and processed by computers to generate a three-dimensional image of the region-of-interest. Due to the requirement of recording a large number of events, coupled with the relatively low detection efficiencies for each radio-nuclide decay, the overall capabilities of both SPECT and PET are limited.

One method to overcome the very low gamma ray throughput of the collimators and the associated increased radiation dose required in SPECT includes electronic collimation. In electronic collimation, Compton scattering is used to reconstruct three-dimensional images from the processing of Compton direction cones of individual gamma rays detected.

An example of implementing electronic collimation for imaging includes a Compton imager that detects multiple Compton scattering interactions in arrays of 1–2 mm thick silicon strip detectors. Specifically, the energies and positions derived from the multiple Compton scattering interactions in the detectors are analyzed for consistency with Compton kinematics to select the correct interaction sequence and thereby determine the most probable incoming direction cone for the gamma ray. Because of the low efficiency of silicon arrays, an alternate electronic collimation imaging concept includes a calorimeter where scattered gamma rays leaving the silicon array are totally absorbed.

Previous Compton imaging concepts are based on operating in a single photon mode. That is, the three-dimensional image reconstruction is achieved by back-projecting Compton direction cones into the presumed source volume and using computer algorithms to reconstruct the morphology of the radioactivity. In this approach, each decay leads to a large conical-shaped annular volume within which the decay occurred.

An alternative Compton imaging concept uses detectors formed of a plurality of thin position-sensitive silicon detector layers. A Compton scattered electron is tracked through two or more layers of the detectors. With this information, the direction of the incident gamma ray can be reduced from a cone to a segment of a cone, with the advantage of improved image reconstruction.

One disadvantage of this alternative Compton imaging system includes a compromise in energy determination of the scattered electron at a first interaction site, and therefore, an associated degradation in the imaging resolution, due to compromised energy resolution in the multiple, thin detector layers. Another significant limitation of this imaging system is the difficulty of tracking electrons with energies below about one MeV due to multiple scattering events. As a result, the most commonly used nuclear medical radio-nuclides cannot be employed by this alternative concept.

A further Compton imager concept uses noble gas detectors. This imager assumes a first interaction that is a Compton scatter event followed by a photoelectric, full energy absorption, at the second interaction site. Advantages of this approach include the use of large volume, position-sensitive detectors, and the moderately good energy resolution. A significant disadvantage is the rather low efficiencies achievable with gas detectors. Another disadvantage is a poorer imaging resolution resulting from the moderate energy resolution of gas detectors.

A limitation relating to most presently available Compton imager concepts is that these devices require that the incident gamma ray energy is totally absorbed. This is necessary to properly determine the direction cone from the Compton scatter formula at the first interaction site. Requiring that the full energy of the incident gamma rays be absorbed will usually result in reduced efficiencies, especially for gamma rays above several hundred keV.

A further limitation of Compton imaging concepts is a "Doppler broadening effect" associated with Compton scattering itself. The Doppler broadening effect results from including the pre-interaction momentum of the electron at the first interaction site, thereby compromising the angular (image) resolution. This effect is significantly worse at lower incident gamma ray energies, and severely compromises image resolution below several hundred keV.

BRIEF SUMMARY OF THE INVENTION

In accordance with the present invention, high-resolution three-dimensional images of regions-of-interest are provided by use of Compton scattering of gamma rays emitted simultaneously or nearly simultaneously (e.g. within one microsecond) by a radio-nuclide. For exemplary purposes, a general case where three gamma rays are emitted simultaneously is used to describe the production of the images. Compton scattering of the gamma rays is detected by a plurality of position-sensitive detectors that provide a scattering medium and are adapted to detect the location of Compton interactions therein. In addition, some or all of the detectors are adapted to measure energy deposited at the interaction sites. Compton direction cones can be determined for each of the three initial gamma rays as a function of detected Compton scattering interactions and the energy losses of the gamma rays at various gamma-ray interaction locations. The intersection of the three conical surfaces of the Compton direction cones defines a limited number of points, one of which is the location of the radio-nuclide decay. Therefore, a single nuclear decay event which emits three coincident gamma rays provides the location of the emitting radio-nuclide. The accumulation of these detected radio-nuclide decay locations on an event-by-event basis permits the three-dimensional imaging of the region-of-interest. Possible uses of the present invention include providing high-resolution three-dimensional images of radio-pharmaceuticals in medical research and clinical applications and Compton medical imagers that limit the dose of radiation to which a patient is exposed.

According to one aspect of the present invention, an imaging device is provided for generating three-dimensional images from a radio-nuclide emitting first, second and third initial gamma rays as simultaneous or nearly simultaneous emissions resulting from a single nuclear decay event. The imaging device comprises a plurality of position-sensitive gamma ray detectors adapted to determine the locations and energy deposits at interaction sites at which gamma rays undergo Compton scatter and photoelectric interactions. A processor determines a radio-nuclide location as a function of (i) at least two energy values corresponding to each of the first, second and third initial gamma rays, (ii) detected locations of first Compton interaction sites of the first, second and third initial gamma rays, respectively, and (iii) detected locations of second interaction sites of Compton scattered gamma rays corresponding to the first, second, and third initial gamma rays, respectively. The at least two energy values are selected from the group consisting of the energy of a respective initial gamma ray, a first deposition energy of the respective initial gamma ray at the respective first interaction site, the energy of the first Compton scattered gamma ray of the respective initial gamma ray, and a second deposition energy of the corresponding Compton scattered gamma ray at the respective second interaction site. The processor generates a three-dimensional image by superposition of individual radio-nuclide locations.

According to another aspect of the present invention, a system is provided for generating three-dimensional images. The system comprises a radio-nuclide emitting first, second and third initial gamma rays as simultaneous or nearly simultaneous emission resulting from a single nuclear decay event and a plurality of position-sensitive gamma ray detectors. Each detector is adapted to determine the locations of Compton interaction sites at which gamma rays undergo Compton scatter interactions. A processor determines a radio-nuclide location as a function of (i) at least two energy values corresponding to each of the first, second, and third initial gamma rays, (ii) detected locations of first interaction sites of the first, second and third initial gamma rays, respectively, and (iii) detected locations of second interactions sites of Compton scattered gamma rays corresponding to the first, second, and third initial gamma rays, respectively. The at least two energy values are selected from the group consisting of the energy of a respective initial gamma ray, a first deposition energy of the respective initial gamma ray at the respective first interaction site, the energy of the first Compton scattered gamma ray of the respective initial gamma ray, and a second deposition energy of the corresponding Compton scattered gamma ray at the respective second interaction site. The processor generates a three-dimensional image by superposition of individual radio-nuclide locations.

According to another aspect of the present invention, an imaging device is provided for generating three-dimensional images by detecting initial gamma rays emitted as simultaneous or nearly simultaneous emissions resulting from a single nuclear decay event of a radio-nuclide. Subsequent Compton scattered gamma rays result from Compton scattering of initial gamma rays, respectively. The imaging device comprises a first position-sensitive detector array for providing a Compton scattering medium for the initial gamma rays to interact at a respective first interaction site in the first-position sensitive detector array and to thereby generate Compton scattered gamma rays, and for detecting a respective location of each first interaction site. A second position-sensitive detector array, surrounding the first position-sensitive detector array, is for detecting a respective location of each respective second interaction site in the second position-sensitive detector array at which the Compton scattered gamma rays interact. A processor determines a radio-nuclide location as a function of (i) at least two energy values corresponding to each of the first, second and third initial gamma rays, (ii) the respective locations of each detected first interaction sites, and (iii) the location of the second interaction site where the Compton scattered gamma ray corresponding to the first initial gamma ray interacts by photoelectric full energy absorption with the second position-sensitive detector array. The at least two energy values are selected from a group consisting of the energy of the respective initial gamma ray, a first deposition energy of the initial gamma ray at the respective first interaction site, the energy of the first Compton scattered gamma ray of the respective initial gamma ray, and a second deposition energy of the respective Compton scattered gamma ray of the first initial gamma ray at the respective second interaction site. The processor generates a three-dimensional image of the region-of-interest by superposition of individual radio-nuclide locations.

According to another aspect of the present invention, a method is provided for generating three-dimensional images. The method comprises the steps of providing a radio-nuclide source generating three initial gamma rays as simultaneous or nearly simultaneous emissions resulting from a single nuclear decay event and using a first position-sensitive detector array to detect locations of three first interaction sites at which the three initial gamma rays respectively interact with the first position-sensitive detector array. Three Compton scattered gamma rays are generated from the three initial gamma rays, respectively, as a result of the three initial gamma rays interacting with the position-sensitive detector array. A second position-sensitive detector array detects locations of three second interaction sites where the three Compton scattered gamma rays interact by full energy deposition with the second position-sensitive detector array, respectively. A radio-nuclide location is determined as a function of (i) at least two energy values corresponding to each of the three initial gamma rays, (ii) the location of each detected first interaction site, and (iii) the location of each detected second interaction site. The at least two energy values are selected from the group consisting of the respective gamma ray energy of the respective initial gamma ray, a first deposition energy of the initial gamma ray at the respective first interaction site, the energy of the first Compton scattered gamma ray of the respective initial gamma ray, and a second deposition energy of the Compton scattered gamma ray at the respective second interaction site. A three-dimensional image is produced by superposition of individual radio-nuclide locations.

In accordance with yet another aspect of the present invention, a method is provided for generating three-dimensional images comprising the steps of providing a radio-nuclide source generating nuclear decay as a positron and a first coincident gamma ray. The positron annihilates with an electron to thereby generate a second gamma ray and a third gamma ray. A first position sensitive detector array detects locations of first, second, and a third gamma ray first interaction sites where the first, second and third gamma rays interact with the first position-sensitive detector array, respectively. A first Compton-scattered gamma ray is generated from the first gamma ray as a result of the first gamma ray interacting with the first position-sensitive detector array. A second position-sensitive detector array detects the location of a second interaction site where the first Compton scattered gamma ray interacts. The energies of the second and third gamma rays are determined to be consistent with 511 keV from the energy losses at the respective first interaction sites and the respective locations of the first and second interaction sites if a Compton scattered interaction occurred at the first interaction site, or from a full energy loss at the first interaction site if a photoelectric interaction occurred at the respective first interaction site. A radio-nuclide location is determined as an intersection of a Compton direction cone corresponding to the first gamma ray and a line connecting the second gamma ray first interaction site and the third gamma ray first interaction site. The three-dimensional images are produced by superposition of individual radio-nuclide locations.

In accordance with another aspect of the present invention, a method is provided for generating three-dimensional images comprising the steps of providing a radio-nuclide source generating nuclear decay as a first coincident gamma ray and a second coincident gamma ray and administering to the radio-nuclide source a thin region-of-interest. A first position-sensitive detector array is used to detect a location of a first gamma ray first interaction site at which the first gamma ray interacts with the first position-sensitive detector array and the location of a second gamma ray first interaction site at which the second gamma ray interacts with the first position-sensitive detector array. A first Compton scattered gamma ray and a second Compton scattered gamma ray are generated from the first gamma ray and second gamma ray, respectively, as a result of the first gamma ray and second gamma ray interacting with the first position-sensitive detector array, respectively. A second position-sensitive detector array is used to detect a first gamma ray second interaction site at which the first Compton scattered gamma ray interacts with the second position-sensitive detector array and a second gamma ray second interaction site where the second Compton scattered gamma ray interacts with the second position-sensitive detector array. A radio-nuclide location is determined as an intersection of a first Compton direction cone corresponding to the first gamma ray, a second Compton direction cone corresponding to the second gamma ray, and the thin region-of-interest. A three-dimensional image is produced by superposition of individual radio-nuclide locations.

In accordance with yet another aspect of the present invention, a system is provided for generating three-dimensional images. This system comprises a radio-nuclide emitting a first, second and third initial gamma ray as simultaneous or nearly simultaneous emission resulting from a single nuclear decay event. A first position-sensitive detector array provides a Compton scattering medium for the first, second and third initial gamma rays to interact to thereby produce first, second and third Compton scattered gamma rays, respectively. The first position-sensitive detector array detects a respective location of each of the first, second and third initial gamma rays at a first, second and third initial gamma ray first interaction site, respectively, in the first position-sensitive detector array. A second position-sensitive detector array surrounds the first position-sensitive detector array and detects locations of the first, second and third Compton scattered gamma rays at a first, second and third Compton gamma ray second interaction site, respectively, in the second position-sensitive detector array. A processor determines a radio-nuclide location as a function of (i) at least two energy values corresponding to each of the three initial gamma rays, (ii) the location of each detected first interaction site, and (iii) the location of the first Compton gamma ray second interaction site. The at least two energy values are selected from the group consisting of the energy of the respective initial gamma ray, a first deposition energy of the initial gamma ray at the respective first interaction site, the energy of the first Compton scattered gamma ray of the respective initial gamma ray, and a second deposition energy of the first Compton scattered gamma ray at the respective second interaction site. The processor generates a three-dimensional image by superposition of individual radio-nuclide locations.

According to another aspect of the present invention, a method is provided for generating three-dimensional images. The method comprises the steps of providing a radio-nuclide source generating three initial gamma rays as simultaneous or nearly simultaneous emissions resulting from a single nuclear decay event and detecting locations of three first interaction sites at which the three initial gamma rays respectively interact with a plurality of position-sensitive detectors. Three Compton scattered gamma rays are generated from the three initial gamma rays, respectively, as a result of the three initial gamma rays interacting with the position-sensitive detector array. The plurality of position-sensitive detectors detect locations of three second interaction sites where the three Compton scattered gamma rays interact with the plurality of position-sensitive detectors, respectively. A radio-nuclide location is determined as a function of (i) at least two energy values corresponding to each of the three initial gamma rays, (ii) the location of each detected first interaction site, and (iii) the location of each detected second interaction site. The at least two energy values are selected from the group consisting of the respective gamma ray energy of the initial gamma ray, a first deposition energy of the initial gamma ray at the respective first interaction site, the energy of the first Compton scattered gamma ray of the respective initial gamma ray, and a second deposition energy of the Compton scattered gamma ray at the respective second interaction site. A three-dimensional image is produced by superposition of individual radio-nuclide locations.

In accordance with yet another aspect of the present invention, a method is provided for generating three-dimensional images comprising the steps of providing a radio-nuclide source generating nuclear decay as a positron and a first coincident gamma ray. The positron annihilates with an electron to thereby generate a second gamma ray and a third gamma ray. A plurality of position-sensitive detectors detect locations of first, second, and a third gamma ray first interaction sites where the first, second and third gamma rays interact with the first position-sensitive detector array, respectively. A first Compton-scattered gamma ray is generated from the first gamma ray as a result of the first gamma ray interacting with the plurality of position-sensitive detectors. One of said plurality of position-sensitive detectors detects the location of a second interaction site where the first Compton scattered gamma ray interacts. The energies of the second and third gamma rays are determined to be consistent with 511 keV from the energy losses at the respective first interaction sites and the respective locations of the first and second interaction sites if a Compton scatter interaction occurred at the first interaction site, or from a full energy loss at the first interaction site if a photoelectric interaction occurred at the respective first interaction site. A radio-nuclide location is determined as an intersection of a Compton direction cone corresponding to the first gamma ray and a line connecting the second gamma ray first interaction site and the third gamma ray first interaction site. The three-dimensional images are produced by superposition of individual radio-nuclide locations.

An important feature of one form of the present invention concerns the use of a radio-nuclide which has three coincident gamma rays produced from a single nuclear decay event. As a result, the reconstructed position for each decay event is limited to a few small volumes of space, typically one to three with a maximum of eight, but with typically one in the region-of-interest.

One advantage of using the coincident Compton device of the present invention is that a collimator is not required. Therefore, the present invention is considerably more efficient than SPECT which typically requires collimators with 0.001–0.01% transmission efficiencies.

An additional advantage of the present invention is the improved imaging resolution as compared with other Compton imager concepts and techniques.

A further advantage of the present invention is that a patient is subjected to a lower dose of radiation during imaging. The combination of high efficiency and much better definition of a possible source location, i.e. volume of space, as compared with SPECT, results in a lower patient dosage while achieving images of similar or improved quality.

A further feature of the present invention is the reduced Compton scattering in the patient. Compton scattering in the patient can limit the imaging capability of nuclear medicine systems. For the widely-used $^{99m}$Tc radio-pharmaceuticals, the gamma ray used has an energy of 140 keV. The probability of Compton scattering of the $^{99m}$Tc gamma rays is about twice that of $^{94}$Tc (a candidate for use as a radio-nuclide in the invention) gamma rays per unit path length in body tissue.

Yet a further feature of the present invention is the higher efficiencies achieved using $^{94}$Tc thereby resulting in image acquisition times reduced by a factor of 1000 compared by $^{99m}$Tc SPECT. As a result, images may be acquired in a reduced time while enabling dynamic imaging of various organ functions such as heart function.

Lower Doppler broadening uncertainty and improved image resolution is provided by the present invention when incorporating the use of high-energy gamma ray lines.

Additional features and advantages of the present invention will be set forth in, or apparent from, the detailed description of preferred embodiments thereof which follows.

DETAILED DESCRIPTION OF THE INVENTION

Figure 1:
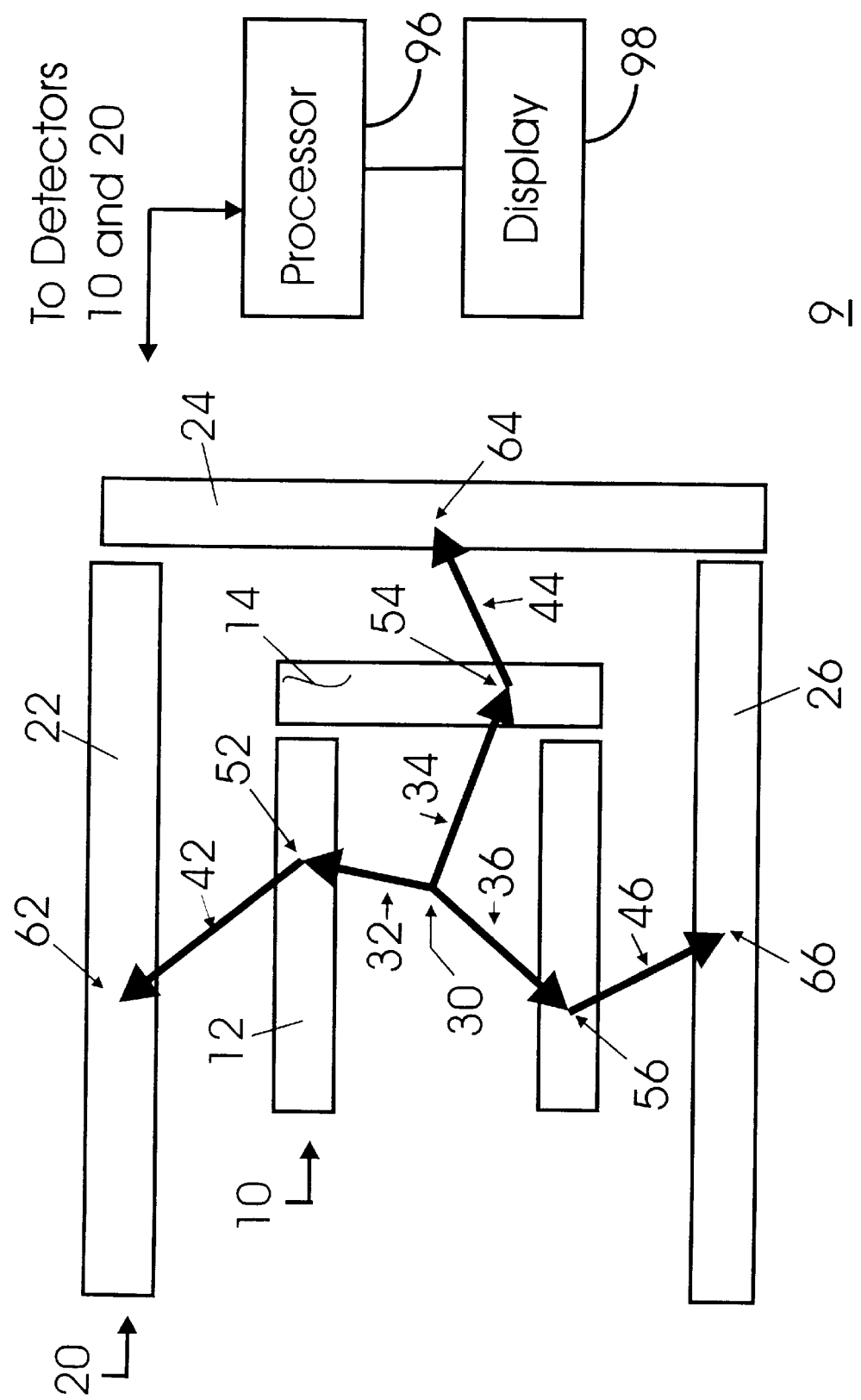
FIG. 1 is a cross sectional view of a coincident Compton imager with detector arrays for detecting three gamma rays according to the present invention.

Referring now to the FIG. 1, depicted therein is a simplified, highly schematic cross sectional view of a Compton imager generally denoted 9. The Compton imager 9 incorporates two gamma ray detector arrays 10, 20. Detector array 10 comprises a cylindrical detector 12 with an end detector 14 disposed at one end of the cylinder detector 12. Detector array 20 comprises a cylindrical detector 22 which is concentric to and surrounds cylindrical detector 12. An end detector 24 is disposed at the end detector array 20 and is located adjacent to end detector 14.

A radio-nuclide, indicated at 30, is characterized by the simultaneous emission of at least three gamma rays 32, 34, 36 associated with each nuclear decay event. Each of the three gamma rays 32, 34, 36 Compton scatters in detector array 10 thereby generating Compton scattered gamma rays 42, 44, and 46, respectively, at first interaction sites 52, 54, and 56, respectively. The Compton scattered gamma rays 42, 44, 46 are fully absorbed in detector array 20 at second interaction sites 62, 64, 66, respectively.

The configurations of detector array 10 and detector array 20 are such that a large solid angle, e.g., greater than $3\pi$ steradians, is subtended by each detector array 10, 20 relative to the region-of-interest or patient.

Several configuration options exist for the types of detectors used. In one configuration, the detector array 10 consists of detectors with excellent position and energy resolution, such as silicon strip detectors. Optimally, the detector array 10 has a 0.5–1 mm three-dimensional position resolution or better and 1–2 keV energy resolution or better. These resolutions can be realized with position-sensitive solid-state detectors such as silicon, germanium, CdZnTe, GaAs and CdTe. Excellent energy resolution in detector array 20 is desirable but not required. When using radio-nuclides that decay with a prompt gamma ray cascade of three or more gamma rays, the detector array 20 preferably provides a high-Z detector, wherein the full energy of the scattered gamma rays leaving the first interaction site is absorbed at the second interaction site via the photoelectric effect.

Numerous radio-nuclides are available for use as radio-nuclide 30. Several radio-nuclides emit three or more gamma rays in a cascade from a high-level nuclear state, and many positron decay radio-nuclides exist which are accompanied by a third gamma ray along with the two 511 keV annihilation gamma rays. An example of a radio-nuclide which emits three or more gamma rays is the nuclide $^{94}$Tc which decays with the emission of gamma rays at 701 keV, 849 keV and 871 keV (along with several lower intensity gamma rays). With a half-life of 298 minutes, and an existing radio-pharmaceutical biochemistry developed for the widely used $^{99m}$Tc radio-pharmaceutical, $^{94}$Tc is well suited for nuclear medical imaging in the Compton imager 9 and alternative configurations of this invention.

An example of a positron decay radio-nuclide that can be used in Compton device 9 is the positron-decay isotope $^{14}$O which has a half-life of 71 sec and produces a gamma ray of energy 2312 keV coincident with the positron emission. $^{14}$O could be used for studies that currently employ $^{15}$O.

Figure 2:
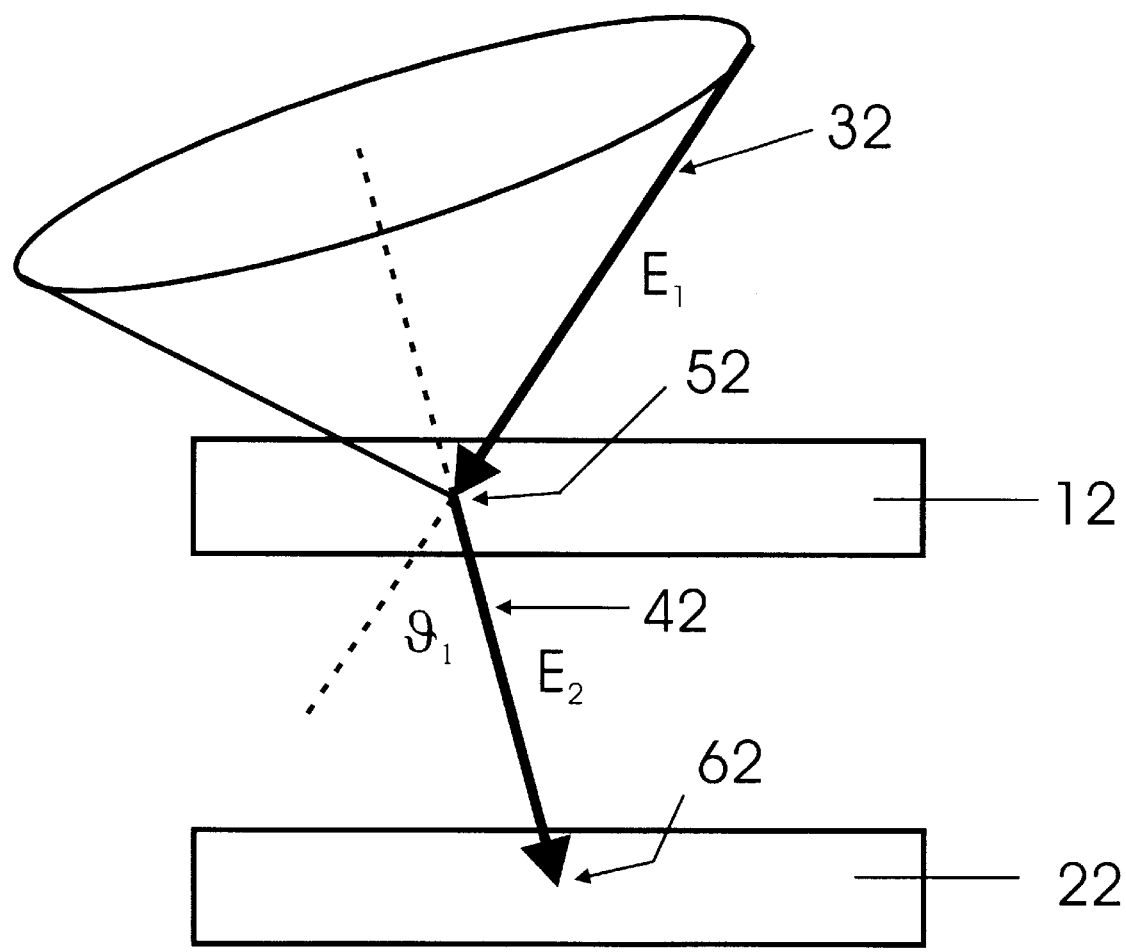
FIG. 2 illustrates the Compton scattering process.

For exemplary purposes, the Compton scattering process for a single gamma ray, gamma ray 32, is illustrated in FIG. 2. A similar Compton scattering process occurs for gamma ray 34 and gamma ray 36.

Referring now specifically to FIG. 2, gamma ray 32 of FIG. 1 is shown incident on detector 12 with an energy $E_1$. Gamma ray 32 undergoes a Compton scatter interaction through angle $\theta_1$ and results in the Compton scattered gamma ray 42 with an energy $E_2$ which is detected in detector 22. The scatter angle is related to the incident gamma ray energy and the scattered gamma ray energy by the Compton formula:

$$\cos\theta_1 = 1 - mc^2\left(\frac{1}{E_2} - \frac{1}{E_1}\right) \tag{1}$$

where $mc^2$ is the rest mass of the electron.

Knowing the locations of the interaction sites 52 in detector 12 and interaction site 62 in detector 22 restricts the direction of the incident gamma ray to lie on a cone of half angle $\theta_1$ whose axis is given by the line joining the interaction site 52 and interaction site 62.

Figure 5A:
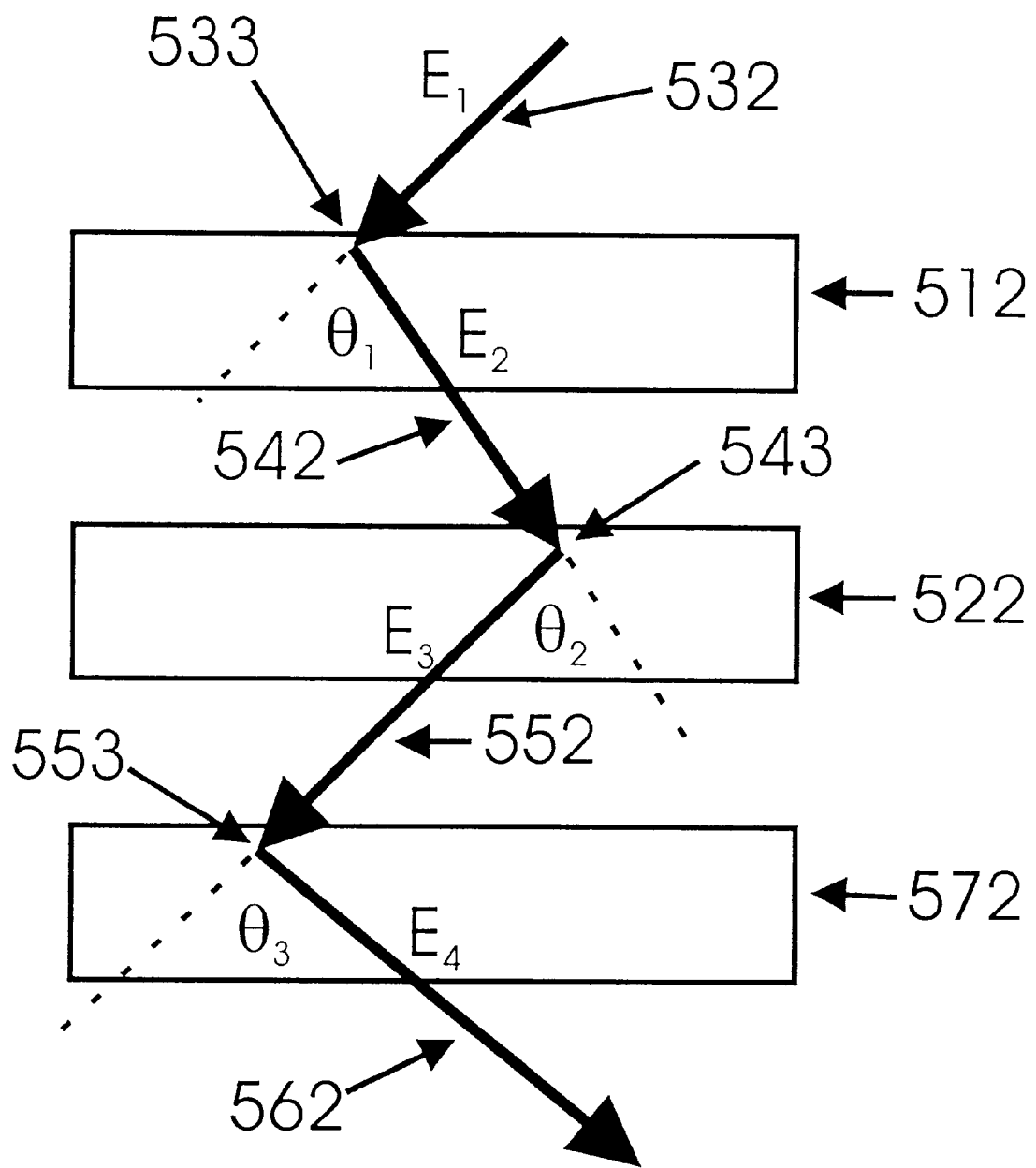
FIG. 5(a) illustrates Compton scattering of a gamma ray at three interaction sites, according to one aspect of the present invention.

Referring back to FIGS. 1 and 2 along with FIG. 5, it will be apparent to one skilled in the art that there are five cases of interaction sequences that are possible.

In case 1, the first interaction of an initial gamma ray is by the photoelectric effect wherein all of the energy of the initial gamma ray is transferred to an electron and is deposited at a single site in a position-sensitive detector. In this case the direction of the initial gamma ray is not determined except in the special circumstance where the gamma ray has an energy of 511 keV and is one of two gamma rays which results from positron-electron annihilation as in a PET imaging embodiment.

In case 2, the initial gamma ray with an unknown energy and direction undergoes a Compton scatter interaction depositing some of its energy, $L_1$, at the first interaction site, and the Compton scattered gamma ray undergoes a photoelectric effect interaction at a second interaction site depositing the remainder of its energy, $L_2$. In this case, the angle of scattering is given by the Compton formula expressed in terms of $L_1$ and $L_2$ as:

$$\cos\theta_1 = 1 - mc^2\left(\frac{1}{L_2} - \frac{1}{L_1 + L_2}\right) \tag{2}$$

In case 3, the initial gamma ray with an unknown energy and direction undergoes a Compton scatter interaction depositing some of its energy, $L_1$, at the first interaction site, and the first Compton scattered gamma ray undergoes a Compton interaction at a second interaction site depositing some of its energy, $L_2$, and the second Compton scattered gamma ray undergoes an interaction at a third interaction site with a known location. As is shown later in [82], the energy of the first Compton scattered gamma ray, $E_2$, can be determined from the energy loss at the second interaction site and the angle of scattering, $\theta_2$, at the second interaction site which is known from the locations of the three interaction sites, and is:

$$E_2 = \frac{L_2}{2} + \left[L_2^2 + \frac{4mc^2 L_2}{1-\cos\vartheta_2}\right]^{\frac{1}{2}} \quad (3)$$

The angle of scatter of the incident gamma ray is then given by:

$$\cos\vartheta_1 = 1 - mc^2 \left(\frac{1}{E_2} - \frac{1}{E_2 + L_1}\right). \quad (4)$$

In case 4 the initial gamma ray with an energy $E_1$ is presumed to be known from a process of elimination wherein all other gamma rays associated with the decay of the radio-nuclide are known. For example, suppose that for an $^{14}O$ decay which emits a 2312 keV gamma ray and two 511 keV gamma rays, that the energies and interaction sequences for the two 511 keV gamma rays have been determined, then the energy of the other coincident gamma ray is also known. This first initial gamma ray undergoes a Compton scatter interaction depositing some of its energy, $L_1$, at the first interaction site, and the respective Compton scattered gamma ray undergoes a second Compton interaction at a second interaction site depositing some of its energy, $L_2$, and the second Compton scattered gamma ray escapes the detector system without further interaction. Then the angle of scattering of the initial gamma ray at the first interaction site is given as:

$$\cos\vartheta_1 = 1 - mc^2 \left(\frac{1}{E_1 - L_1} - \frac{1}{E_1}\right) \quad (5)$$

In case 5, an alternative to case 4, the initial gamma ray with an energy $E_1$ is presumed to be known from a process of elimination wherein all other gamma rays associated with the decay of the radio-nuclide are known. For example, suppose that for an $^{14}O$ decay which emits a 2312 keV gamma ray and two 511 keV gamma rays, that the energies and interaction sequences for the two 511 keV gamma rays have been determined, then the energy of the other coincident gamma ray is also known. This third initial gamma ray undergoes a Compton scatter interaction depositing an unknown energy at the first interaction site, and the Compton scattered gamma ray undergoes full energy absorption at a second interaction site depositing its energy, $L_2=E_2$, or alternatively undergoes a series of interactions from which the energy of the first Compton scattered gamma ray can be determined as in [58] above. Then the angle of scattering of the initial gamma ray is given as:

$$\cos\vartheta_1 = 1 - mc^2 \left(\frac{1}{E_2} - \frac{1}{E_1}\right) \quad (6)$$

From the foregoing, it will be apparent to one skilled in the art that in the cases given above, the angle of Compton scattering at the first interaction site can be determined when at least two values of the energies selected from the group consisting of the initial gamma ray energy, a first deposition energy of the initial gamma ray at the first interaction site, the first Compton scattered gamma ray energy, and a second deposition energy of the Compton scattered gamma ray at the second interaction site, are known. With knowledge of two of these energies, the angle of Compton scattering at the first interaction site can be determined.

Referring back to FIG. 1, along with FIG. 2, each of the three gamma rays 32, 34, 36 has a respective initial energy $E_1$. The first interaction of gamma ray 32 is at the interaction site 52 in the detector array 10 where the gamma ray 32 undergoes a Compton scatter interaction in which some energy, $L_1$ is lost and Compton scattered gamma ray 42 leaves with an energy $E_2=E_1-L_1$. The Compton scattering formula relates the angle of scatter with the energies of the incident (e.g., initial gamma ray 32) and exiting gamma ray (e.g., Compton scattered gamma ray 42). In applications where the energy of the incident gamma rays are known, e.g. nuclear medicine, a precise determination of the energy loss, $L_1$, in detector array 10 also determines the scatter angle $\theta_1$. Hence, the radio-nuclide producing the gamma ray must have originated on the surface of the cone. Stated more precisely, the gamma ray must have originated on the surface of a conical shell due to the uncertainty in the scatter angle. Thus, the path of each gamma ray 32, 34, 36 lies on a conical surface similar to the one as shown in FIG. 2.

Figure 3:
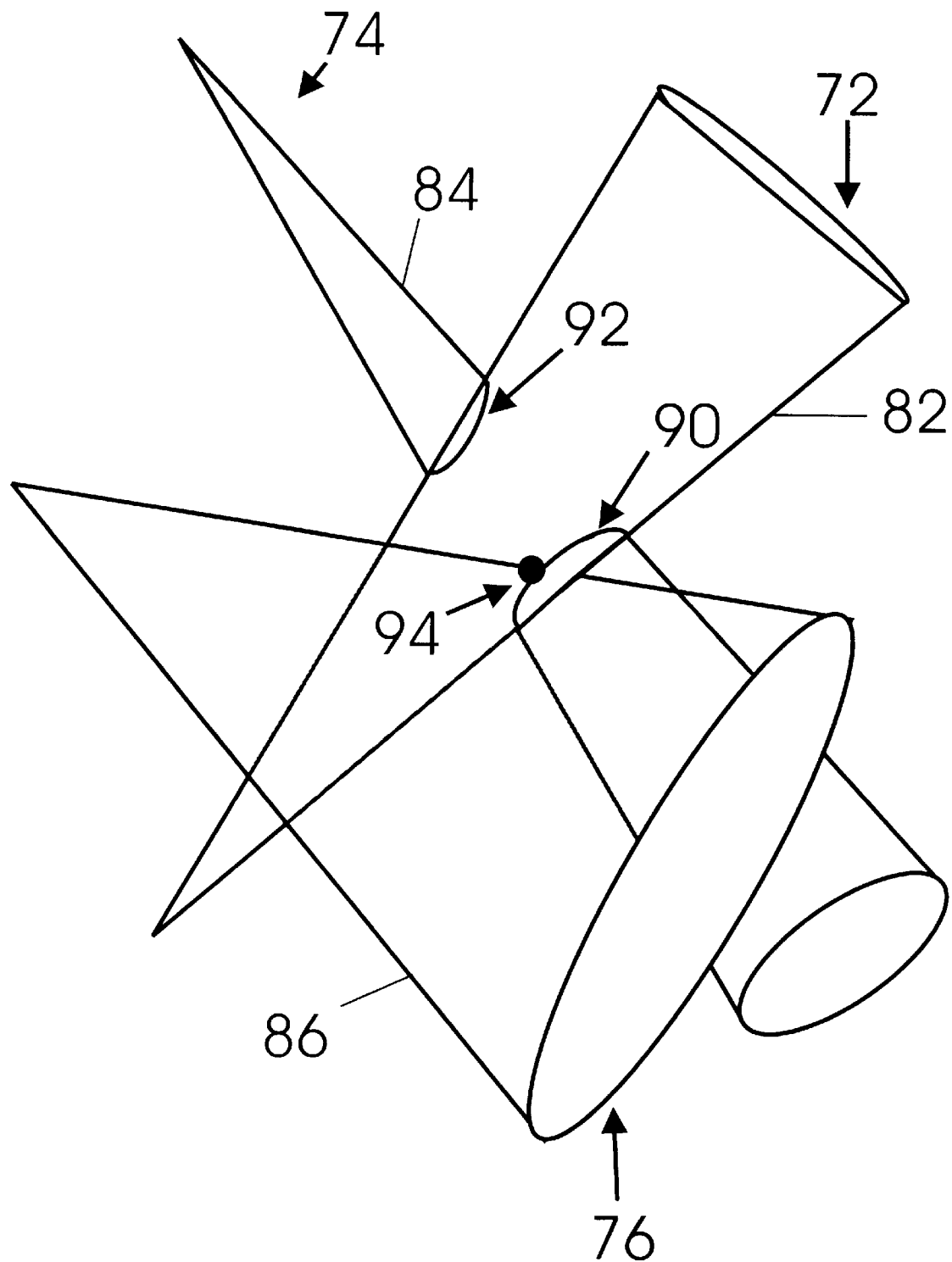
FIG. 3 is a schematic of three intersecting Compton direction cones and the points common to all three cones for the three gamma rays of FIG. 1.

Referring now to FIG. 3, depicted therein are three Compton direction cones 72, 74, 76 with conical surfaces 82, 84, 86 corresponding to the initial gamma-rays 32, 34, 36 respectively. The conical surface 84 of Compton direction cone 74 intersects the conical surface 82 with common points of the two cones 72, 74, lying on two curved lines 90, 92. The direction cone 76 intersects curved lines 90, 92 at location 94. Location 94 may represent one or two points whereby, the intersection of these three conical surfaces 82, 84, 86 defines a limited number of points, one of which is the location of the radio-nuclide decay from radio nuclide 30.

A reconstructed position for each decay event is limited to a few small volumes of space, typically one to three, with a maximum of eight, and with typically only one in the region-of-interest. These volumes are the common volumes of the three intersecting conical surfaces 82, 84, 86 and are limited to those volumes contained within the patient or other possible source region.

The accumulation of various locations corresponding to location 94 on a nuclear decay event-by-event basis permits the three-dimensional imaging of a region-of-interest, without the need for re-construction from a large number of events as required with SPECT and PET, and with spatial resolution limited by the physics of the Compton scattering process.

One method of determining a location corresponding to location 94 utilizes a processor 96 (shown in FIG. 1) to evaluate the Compton formula (1) for each gamma ray 32, 34, 36 so as to determine a possible origin of the respective gamma ray. The location of the nuclide 30 from which the gamma rays 32, 34, 36 are emitted is a point defined as, $x_0$, $y_0$, $z_0$ in a Cartesian coordinate system. The first gamma ray 32 has an interaction site 52 defined as $x_{11}$, $y_{11}$, $z_{11}$ and the scattered gamma ray 42 has an interaction site 62 defined as $x_{12}$, $y_{12}$, $z_{12}$.

By the law of cosines:

$$A^2 B^2 + C^2 + 2BC \cos\theta_1 \quad (7)$$

where:

$$A^2 = (x_{12}-x_0)2+(y_{12}-y_0)^2+(z_{12}-z_0)^2 \quad (8)$$

$$B^2 = (x_{12}-x_{11})^2+(y_{11}-y_{11})^2+(z_{12}-z_{11})^2 \quad (9)$$

$$C^2 = (x_{11}-x_0)^2+(y_{11}-y_0)^2+(z_{11}-z_0)^2 \quad (10)$$

and $\theta_1$ is the Compton scatter angle.

A similar equation can be written for the initial gamma ray 34 and the initial gamma ray 36. Using the three equations, the three unknown variables $x_0$, $y_0$, and $z_0$ are computed by processor 96.

Another method for determining the location corresponding to location 94 uses processor 96 to evaluate each small volume element (voxel) in the region of interest for each gamma ray 32, 34 and 36 so as to determine a common possible origin for the respective gamma rays. For each gamma ray, Compton formula (1) is evaluated to determine a direction cone based on the line joining the locations of the first and second interactions of the respective gamma rays 32, 34 and 36, and the respective Compton scatter angles at their respective first interaction locations. The uncertainty in each scatter angle is determined as discussed below and these uncertainties are used to define respective conical shell volumes as the region of space consistent with the possible origin of each respective gamma ray 32, 34 and 36. The three-dimensional region-of-interest is divided into small volume elements (voxels). The central point of each voxel is determined to either lie within or without the conical shell volume for each respective gamma ray 32, 34 and 36. The voxel(s) that is consistent with all three conical shell volumes is determined to be the possible location(s) of the radio-nuclide decay.

Figure 4A:
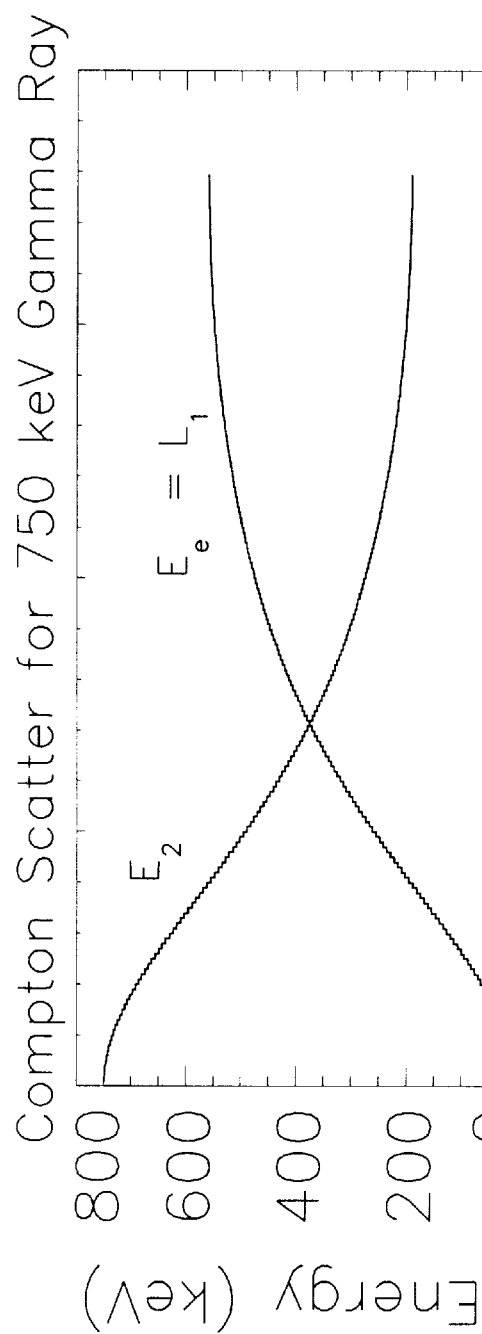
FIG. 4(a) is a plot of scattered gamma ray energy $E_2$ versus angle for an incident gamma ray of 750 keV.
Figure 4B:
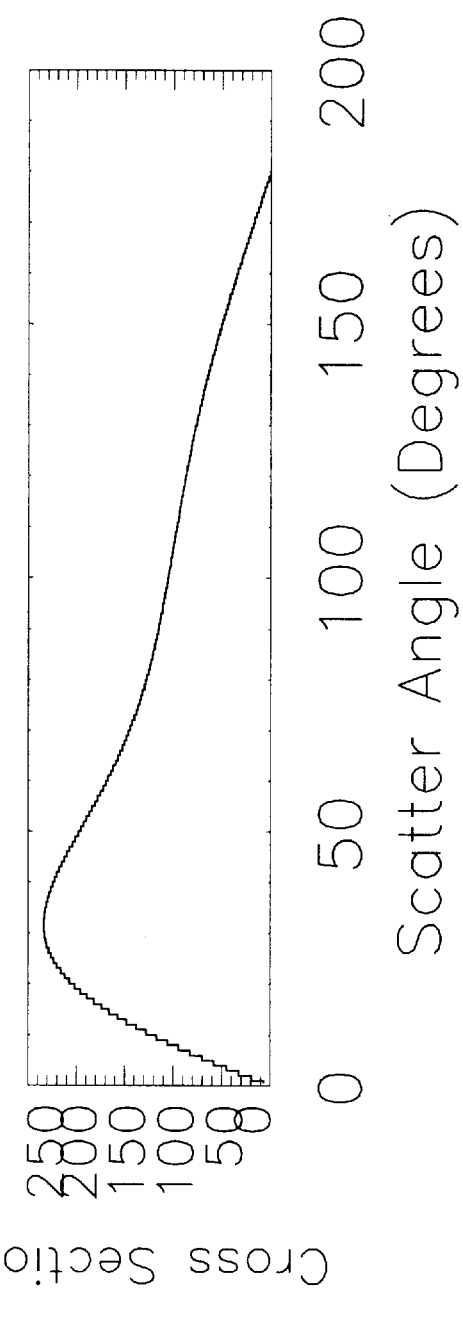
FIG. 4(b) is a plot of the Compton scatter cross-section (relative) as a function of scattered angle for an incident gamma ray with energy of 750 keV.
Figure 4C:
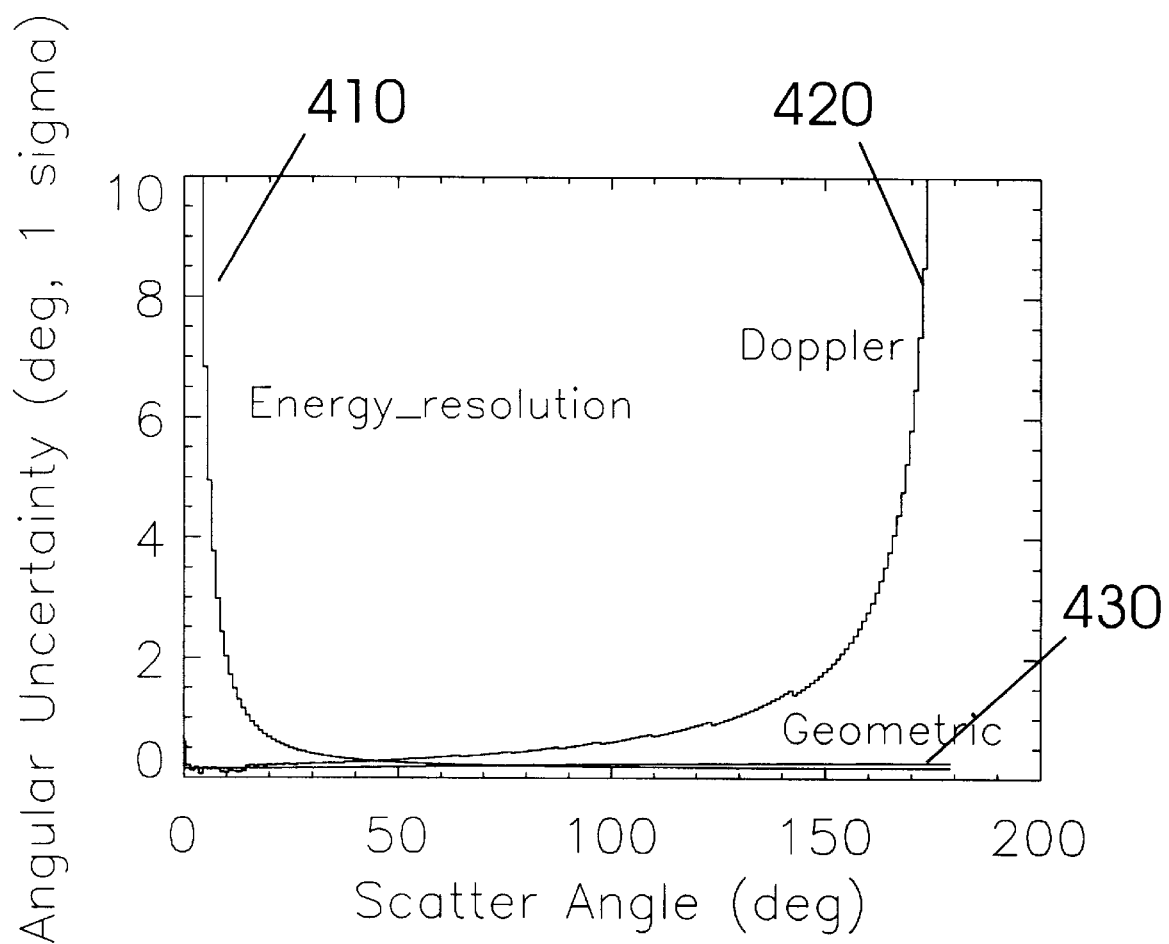
FIG. 4(c) is a plot of angular uncertainty versus scattering angle of a gamma ray indicating components due to energy resolution, Doppler broadening, and position resolution (geometry)

To facilitate further understanding of how processor 96 determines location 94, reference will be made to FIGS. 4(*a*) and 4(*b*). FIG. 4(*a*) is a plot of the energy $E_2$ of Compton scattered gamma ray 42 and the energy loss, $L_1 = E_e$, to an electron at the scatter site 52 as a function of the Compton scattering angle and for an initial gamma ray energy of 750 keV. The Compton scatter cross section shown in FIG. 4(*b*) has a broad peak for scattering angles between approximately 15° and 100°. For these scattering angles, the energy loss at the Compton scatter site in the detector array 10 ranges from approximately 30–500 keV for incident gamma rays of 700 to 900 keV. The uncertainty in the scattering angle is given by:

$$d\vartheta_1 = \frac{mc^2}{\sin\vartheta_1}\left[\left(\frac{1}{(E_1-L_1)} - \frac{1}{E_1^2}\right)^2 dE_1^2 + \frac{dL_1^2}{(E_1-L_1)^4}\right]^{\frac{1}{2}} \quad (11)$$

where $dE_1$ is the error determined in the initial gamma ray energy and $dL_1$ is the error in the energy deposited at the first interaction site.

The error in the scattering angle determines the angular thickness of the Compton annular conical shell 72 from which the incident gamma ray 32 must have originated. The angular spread is determined by the energy resolution of the detector array 10 and 20, and the precision with which the interactions are located in detector array 10 and detector array 20. It is also dependent on the scattering angle and the energy of the incident gamma ray. An advantage of using higher-energy gamma rays is that a better angular resolution is realized using the Compton scatter technique.

Another limitation on the angular spread is an effect due to the motion of an atomic electron at the interaction site in detector array 10. Eqs. (1), (2), (3), (4), (5), and (6) are calculated assuming the electron is at rest. However, atomic electrons that scatter the gamma rays do have velocities, and as a result, an additional error, known as the Doppler broadening uncertainty, is introduced in the incident gamma ray direction. The angular uncertainty associated with this Doppler effect is less severe for higher-energy gamma rays and for Compton scattering off lower-Z nuclei. Because of the Z-dependence of the Doppler broadening, imaging performance will be better using low-Z silicon detectors for the detector array 10 rather than high-Z detectors such as germanium or CdZnTe.

FIG. 4(*c*) shows the uncertainty in the scatter angle due to the Doppler broadening effect 420, the energy resolution of the detectors 410, and the uncertainties in the position of the gamma ray interactions 430 for a 750 keV gamma ray as a function of scatter angle. For the scatter angles with highest scatter probability of 15° to 100°, as seen in FIGS. 4(*a*) and 4(*b*), it will become apparent in FIG. 5 to one of ordinary skill, that the uncertainty in the scatter angle is about 0.5° for a Compton direction cone which corresponds to an incident gamma ray with energies comparable to those associated with $^{94}$Tc decay. It will be apparent to those skilled in the art that the image resolution is dependent on the uncertainty in the scattering angle at the respective first interaction sites, the uncertainty in the location of the interactions at the respective first interaction sites, and the distance from the respective first interactions sites to the radio-nuclide region.

The processor 96 renders three-dimensional images by accumulating individual radio-nuclide locations and then superposing the locations. Subsequently, the processor 96 provides the three-dimensional images on a display 98 for viewing.

Several alternative configurations exist for the position-sensitive gamma ray detector arrays to be employed by a Compton imager comprising the present invention. A first alternative detector configuration includes a first detector array with excellent spectral and spatial resolution and a second detector array with high spatial resolution but modest energy resolution. For example, the second detector array could be a position-sensitive scintillation detector array such as a traditional SPECT scintillation camera. Assignment of the incident photon energy is made based on the modest scintillator energy resolution and consistency with the known gamma ray energies emitted from the source. As an example, using the $^{94}$Tc decay, a system using scintillation cameras as the second detector array would generally provide good discrimination between the 701 keV gamma rays and the two higher energy gamma rays at 849 keV and 871 keV, but would not provide clear discrimination between the 849 and 871 keV gamma rays due to the approximately 40 keV energy resolutions of the scintillation detector array. In this case, two positions for the location of the radio-nuclide source would be determined: one position with high probability assuming the correct identification for the two high-energy gamma rays and a second position with low probability assuming the incorrect identification. The second position would be offset by a small location, e.g. one to two cm. The net effect in the full image reconstruction would be a true image surrounded by a halo.

A second alternative detector configuration utilizes a first detector array that provides good position resolution and a second detector array that provides both good spectroscopy and position resolution along with a high efficiency for detection of the scattered gamma ray. High-Z solid-state detectors, e.g. germanium, are desired in this configuration by placing the requirement for the high-spectral resolution detector in the second detector array where the energy of the incoming gamma ray is less and the full energy detection efficiency can be enhanced.

In this second alternative detector configuration, the first detector array could utilize detectors with excellent position resolution but which lack energy resolution. For example, the first detector array could be constructed of crossed (orthogonal) plastic scintillator fiber arrays. In such detectors with fiber cross sections of 0.25 mm, the Compton scattered electron could transit two or more orthogonal fibers and provide excellent position resolution in the first detector array. Coupled with the low Doppler broadening associated with these low-Z scintillators, this second alternative detector configuration may be optimal for certain imaging applications.

In a third alternative detector configuration, a Compton imager incorporates high-spectral resolution and high spatial resolution detectors distributed more uniformly in distance from the subject (e.g. the patient). This configuration offers several advantages. The energy of the incident gamma ray is determined from the energy losses at the first two interaction sites and the angle of scattering at the second site. Consequently, potential ambiguity between two gamma rays with similar energies would be removed. Further, this configuration would provide the highest attainable efficiency for a Compton imaging instrument. In addition, this embodiment enables the use of low-Z detectors such as silicon strip detectors for all detector elements.

In this alternative embodiment, the Compton imager determines the location of a radio-nuclide by detecting three or more interaction sites for each of the three coincident gamma rays emitted. To enable a better understanding of this embodiment, reference is made to FIGS. 5(a) and 5(b). Briefly, a Compton imager 509 includes a detector array 510 formed of a plurality of detector layers. The detectors preferably have good position resolution and good energy resolution, e.g., a position resolution of 0.5–1 mm and an energy resolution of 1–2 keV. A processor 596 computes the location of radio-nuclide 530 as within region-of-interest 594. By determining the location of multiple decay events, three-dimensional images are rendered on a display 598.

The Compton imager 509 can determine the energy and direction angle of each gamma ray 532, 534, 536 from only the partial energy loss at the first three interaction sites if the first two interactions are Compton scatters. For example, gamma ray 532 with energy, $E_1$, is incident on a detector 512. The gamma ray 532 incurs at least two successive Compton scatter interactions. A first interaction is in the detector 512 at interaction site 533 producing a first Compton gamma ray 542 with energy $E_2$. A second interaction is in detector 522 at interaction site 543, resulting in a second Compton gamma ray 552 having energy $E_3$. The gamma ray 532 incurs a third interaction, i.e. the interaction of Compton gamma ray 552 in detector 572 at interaction site 553, resulting in a gamma ray 562 having energy, $E_4$. Gamma ray 562 is not detected but escapes from the detector array 510. Nevertheless, even though the full energy of the initial gamma ray 532 is not deposited in the detector array 510, the energy of initial gamma ray 532 can be determined as follows.

$E_1$, $E_2$, and $E_3$ are the incident photon energies for each scattering, and $\theta_1$, $\theta_2$, are the scatter angles at the first two interaction sites. The Compton scattering formulae for the first two interactions are:

$$\cos\vartheta_1 = 1 - mc^2\left(\frac{1}{E_2} - \frac{1}{E_1}\right) \quad (12)$$

$$\cos\vartheta_2 = 1 - mc^2\left(\frac{1}{E_3} - \frac{1}{E_2}\right) \quad (13)$$

where $L_1$, and $L_2$ are the energy losses to the scattered electrons at the first and second interaction sites and are:

$$L_1 = E_1 - E_2 \quad (14)$$

$$L_2 = E_2 - E_3 \quad (15)$$

Solving (15) for $E_3$ and substituting into (13) yields a quadratic equation with $E_2$ as the only unknown, since $\theta_2$ is determined from the locations of the three interactions. Thus processor 596 can compute the energy $E_2$ using equation (3).

The incident gamma ray energy, $E_1$ is also determined from (5), and is given by:

$$E_1 = L_1 + \frac{L_2}{2} + \frac{1}{2}\left[L_2^2 + \frac{4\,mc^2 L_2}{1 - \cos\vartheta_2}\right]^{\frac{1}{2}} \quad (16)$$

where $mc^2$ is the rest mass of the electron.

The processor 596 makes similar computations for the remaining two gamma rays, 534, 536. From the computed energies and scatter angles from all three gamma rays 532, 534, 536, the processor 596 determines the origin of the gamma rays, and therefore a possible location of radio-nuclide 530, to be a location in region-of-interest 594. Three-dimensional images are rendered by processor 596 and viewed on display 598 from the superposition of individual radio-nuclide locations in 594.

One advantage of this embodiment is that the addition of detecting and processing data from a third interaction for each gamma ray provides independent determination of the energy of each of the initial gamma rays without the necessity of full energy deposition in the detector array. It also provides for acceptance of the full range of scatter angles at the first interaction site. As a result, this embodiment provides for high-efficiency and improved imaging with a lower patient dose.

Figure 6A:
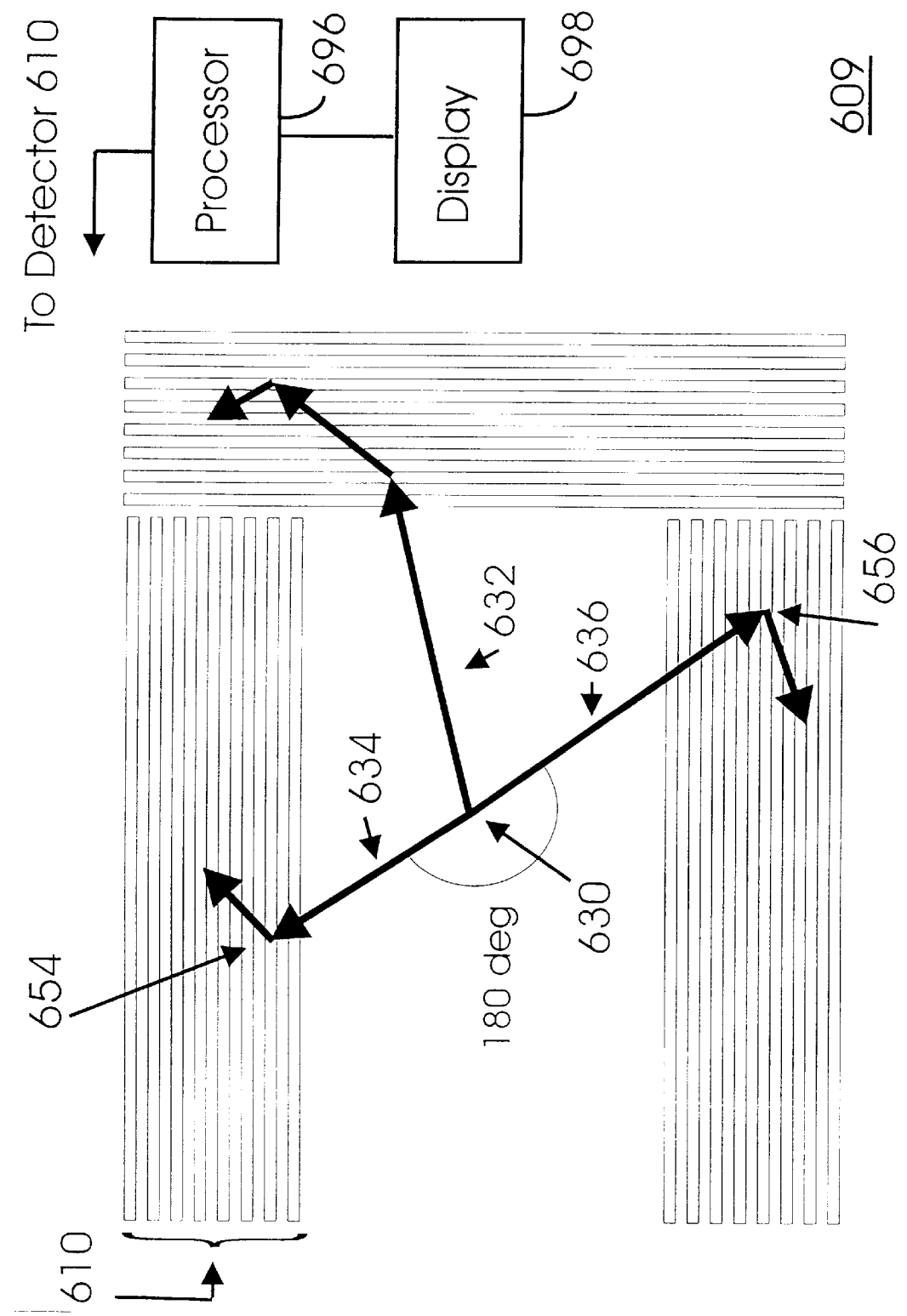
FIG. 6(a) is a cross sectional view of a Compton imager which utilizes the gamma rays from a positron emitter that produces two 511 keV gamma rays and a third coincident gamma ray.
Figure 6B:
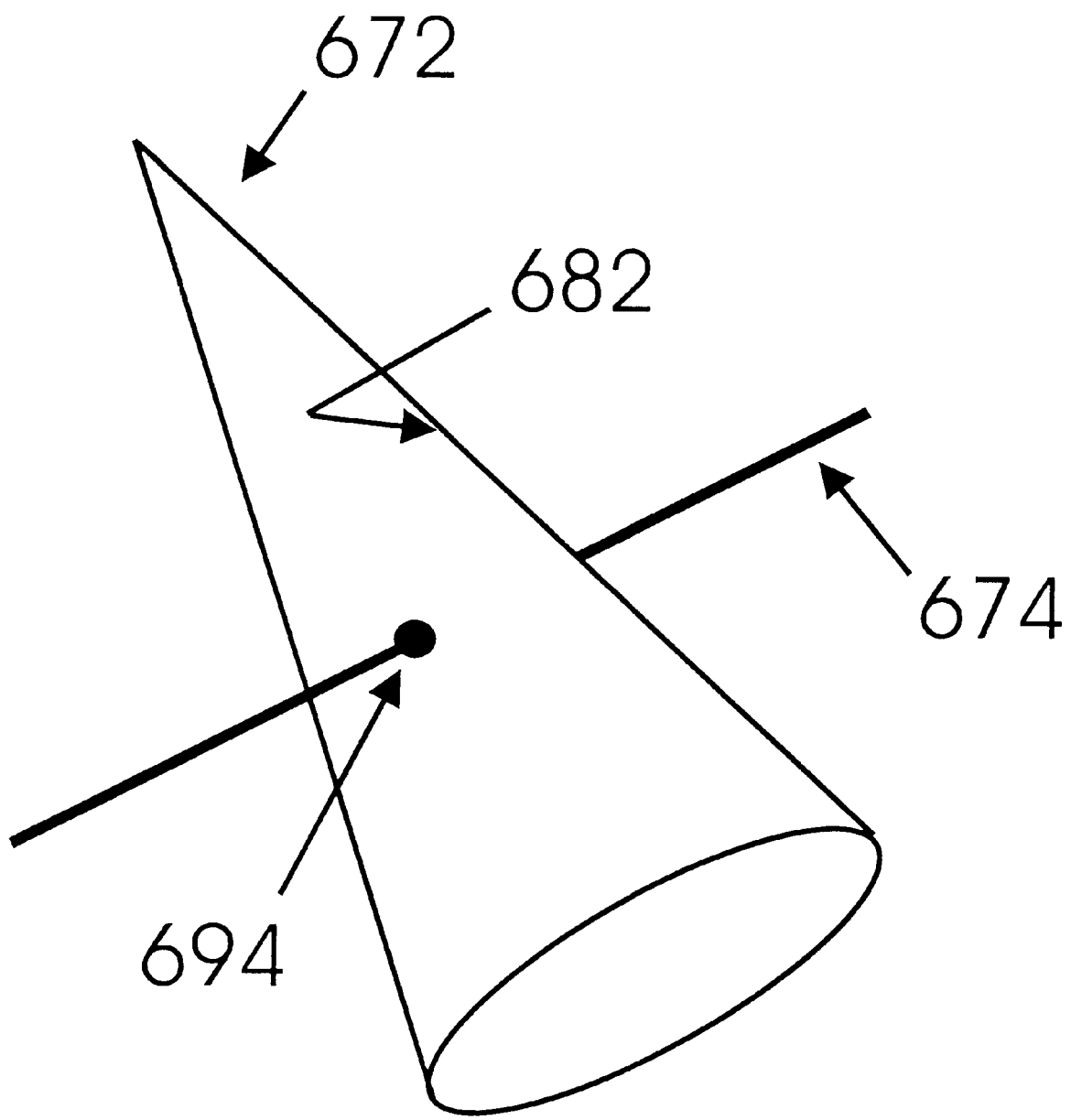
FIG. 6(b) is a schematic of the intersection of a Compton direction cone corresponding to the coincident gamma ray and a line joining the first interaction sites for each of the 511 keV gamma rays of FIG. 6(a)

Referring now generally to FIGS. 6(a) and 6(b), in an alternative embodiment, a Compton imager 609 utilizes a positron-decay nuclide with one or more additional gamma rays in addition to the two 511 keV annihilation gamma rays. A partial list of positron-decay radio-nuclides that are accompanied by a coincident gamma ray which can be used with the Compton imager 609 are provided in Table 1. As will be apparent to one skilled in the art, a wide range of radio-pharmaceuticals, including high energy gamma ray emitters, are available for use in Compton imager 609.

TABLE 1

| Isotope | Halflife | Gamma ray energy (keV) | Branching ratio | Comment |
|---|---|---|---|---|
| $^{10}$C | 19s | 511 | 200% | |
| | | 717 | 100% | |
| $^{14}$O | 70s | 511 | 200% | |
| | | 2312 | 99% | |
| $^{34m}$Cl | 32m | 511 | 200% | |
| | | 145 | 45% | |
| | | 1170 | 12% | |
| | | 2120 | 38% | |
| $^{38}$K | 7m | 511 | 200% | |
| | | 2170 | 100% | |
| $^{42m}$Sc | 60S | 511 | 200% | 5 coin.γ's |
| | | 438 | 100% | |
| | | 1220 | 100% | |
| | | 1520 | 100% | |
| $^{43}$Sc | 3.92h | 511 | 176% | |
| | | 375 | 22% | |
| $^{44}$Sc | 3.92h | 511 | 188% | |
| | | 1159 | 100% | |
| $^{48}$V | 16d | 511 | 200% | 4 coin.γ's |
| | | 983 | 100% | |
| | | 1132 | 97% | |
| $^{50}$Mn | 2m | 511 | 198% | 5–6 coin.γ's |
| | | 783 | 100% | |
| | | 1110 | 100% | |
| | | 1280 | 25% | |
| | | 1450 | 75% | |
| $^{52m}$Mn | 21m | 511 | 193% | |
| | | 1434 | 100% | |
| $^{53}$Fe | 8m | 511 | 196% | |
| | | 380 | 32% | |

TABLE 1-continued

| Isotope | Halflife | Gamma ray energy (keV) | Branching ratio | Comment |
|---|---|---|---|---|
| $^{54}$Co | 18h | 511 | 160% | |
| | | 410 | 100% | |
| | | 1140 | 100% | |
| | | 1410 | 100% | |
| $^{55}$Co | 18h | 511 | 160% | |
| | | 930 | 80% | |
| $^{56}$Co | 77d | 511 | 40% | |
| | | 847 | 100% | |
| | | 1238 | 66% | |
| $^{60}$Cu | 23m | 511 | 186% | |
| | | 1332 | 80% | |
| | | 176? | 52% | |
| $^{66}$Ga | 9.5h | 511 | 114% | |
| | | 1039 | 37% | |
| $^{67}$Ge | 18m | 511 | 170% | |
| | | 1700 | 105% | |
| $^{70}$As | 52m | 511 | 183% | |
| | | 1040 | 78% | |
| $^{73}$Se | 7.1h | 511 | 130% | |
| | | 359 | 99% | |

A partial list of radio-isotopes that emit three or more simultaneous gamma rays and have suitable half-lives that are candidates for use in Compton coincident imaging is given in Table 2.

TABLE 2

| Isotope | Half-life | Gamma ray energy (keV) | Branching ratio |
|---|---|---|---|
| $^{28}$Mg | 21.2h | 310 | 96% |
| | | 400 | 30% |
| | | 950 | 30% |
| | | 1350 | 70% |
| $^{37}$Cl | 55m | 246 | 44% |
| | | 1270 | 50% |
| | | 1520 | 42% |
| $^{43}$K | 22.4h | 220 | 3% |
| | | 373 | 85% |
| | | 390 | 18% |
| | | 590 | 135 |
| $^{48}$Sc | 1.83d | 175 | 6% |
| | | 983 | 100% |
| | | 1040 | 100% |
| | | 1314 | 100% |
| $^{50}$Sc | 1.72m | 520 | 100% |
| | | 1120 | 100% |
| | | 1550 | 100% |
| $^{55}$V | 55s | 840 | 100% |
| | | 990 | 100% |
| | | 2210 | 100% |
| $^{56}$Mn | 2.57h | 847 | 99% |
| | | 1811 | 29% |
| | | 2110 | 15% |
| $^{56}$Ni | 6.1d | 163 | 99% |
| | | 276 | 31% |
| | | 472 | 35% |
| | | 748 | 48% |
| | | 812 | 85% |
| | | 1560 | 145 |
| $^{71m}$Zn | 4h | 385 | 94% |
| | | 495 | 75% |
| | | 609 | 65% |
| $^{82}$Br | 35h | 554 | 66% |
| | | 619 | 41% |
| | | 698 | 27% |
| | | 777 | 83% |
| | | 828 | 25% |
| | | 1044 | 29% |
| | | 1317 | 26% |
| | | 1475 | 17% |

TABLE 2-continued

| Isotope | Half-life | Gamma ray energy (keV) | Branching ratio |
|---|---|---|---|
| $^{84}$Br | 6m | 440 | 68% |
| | | 880 | 75% |
| | | 1460 | 75% |
| | | 1890 | 16% |
| $^{94}$Tc | 293m | 511 | 22% |
| | | 701 | 100% |
| | | 849 | 100% |
| | | 871 | 100% |
| $^{94m}$Tc | 53m | 511 | 132% |
| | | 871 | 91% |
| | | 1530 | 10% |
| | | 1870 | 9% |
| $^{130}$I | 12.5h | 419 | 35% |
| | | 538 | 99% |
| | | 669 | 100% |
| | | 743 | 87% |
| | | 1150 | 12% |

Where SPECT is typically limited to radio-nuclides that have low-energy gamma rays due to the difficulty of manufacturing good collimators for gamma rays above 200–300 keV, the present Compton imager does not have such a limitation.

One preferable positron emitting radio-nuclide is $^{14}$O. $^{14}$O has a short half-life: 71 seconds. The two 511 keV gamma rays are accompanied by a third gamma ray with an energy of 3212 keV. The use of $^{14}$O in this embodiment will enable clinical studies that are currently obtained with $^{15}$O, a positron-emitting isotope with a half-life of 123 seconds. The advantage will be the improved imaging achieved from locating each decay to a point rather than a line in the region-of-interest.

A second preferable positron-emitter radio nuclide is $^{94}$Tc. $^{94}$Tc has a useful half-life of approximately five hours, and emits gammma rays of 701 keV, 849 keV and 871 keV with each decay event. In addition to these three gamma rays, 511 keV gamma rays associated with positron annihilation are emitted about 22% of the time. In addition, there is a decay from an isomeric level that provides coincident 511 keV gamma rays 62% of the time and a 871 keV gamma ray. $^{99m}$Tc is a widely-used radio-nuclide in nuclear medicine so that a broad range of nuclear medicine applications presently exist. Much of the chemistry for the production of $^{99}$Tc-labeled radio-pharmaceuticals will be directly applicable to the use of $^{94}$Tc and $^{94m}$Tc-labeled radio-pharmaceuticals.

Referring now specifically to FIGS. 6(*a*) and 6(*b*), Compton imager 609 uses a positron-emitting radio-nuclide 630 that also has a gamma ray 632 coincident with the positron, resulting in three gamma rays being emitted nearly simultaneously: the two 511 gamma rays 634, 636 from the positron annihilation and the coincident decay gamma ray 632. Compton imager 609 operates in a PET mode for detection of the two 511 keV gamma rays 634, 636 at interaction sites 654 and 656, respectively. From the location of these interaction sites, the processor 696 determines a line of emission 674 along which the decay occurred.

In addition, the Compton imager 609 operates in a similar detection mode as Compton imager 9 to detect the coincident gamma ray 632 and to determine a possible origin of gamma ray 632. Subsequently, the processor 696 determines a nuclide location 694 as the intersection of line 674 and a conical surface 682 of Compton scatter cone 672, the Compton direction cone corresponding to gamma ray 632. Three-dimensional images are rendered by processor 696 and viewed on display 698 from the superposition of individual radio-nuclide locations.

Figure 7:
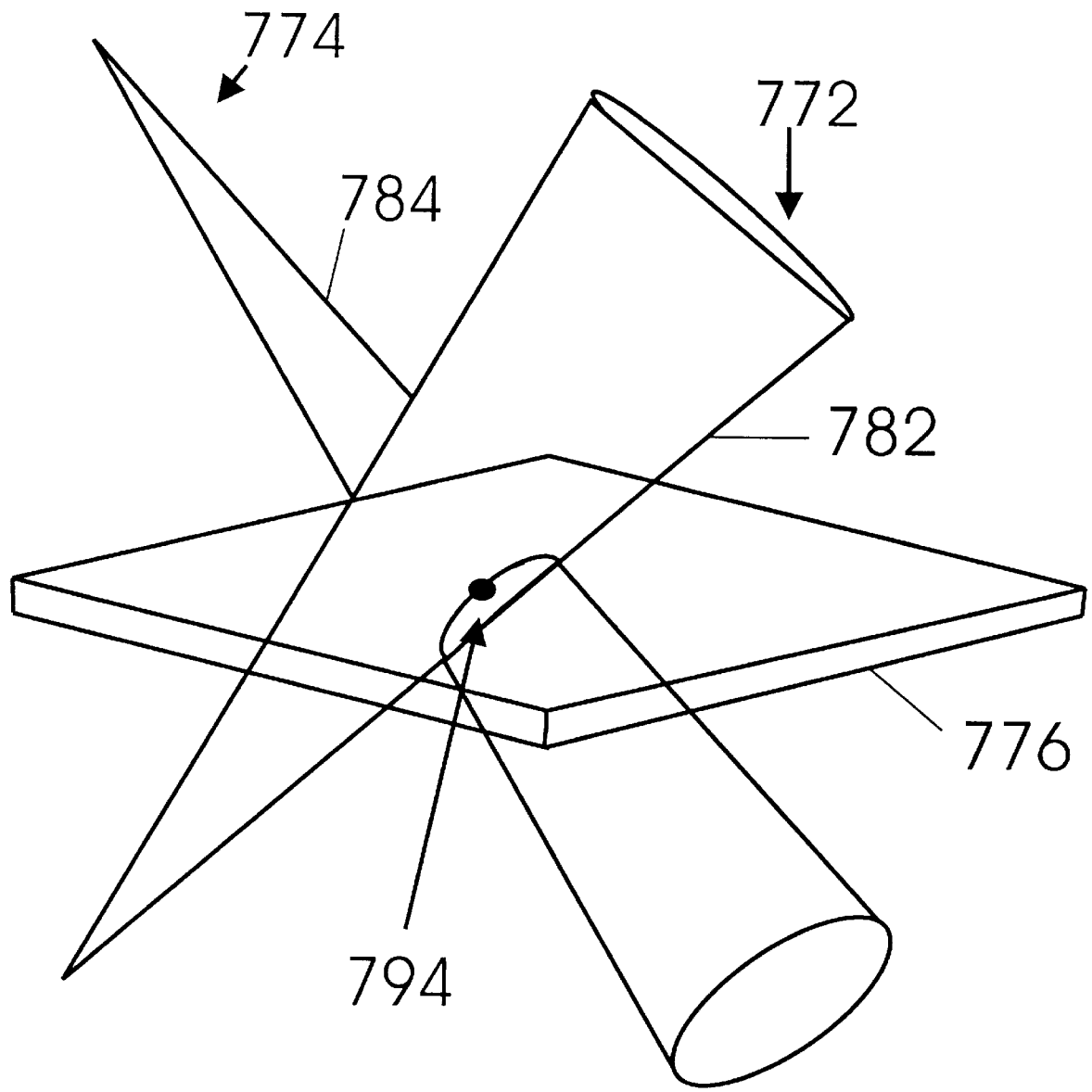
FIG. 7 is a schematic of the intersection of two Compton direction cones and a thin layer sample.

Discussion of yet another alternative embodiment is provided with reference to FIG. 7. A Compton imager is used to image a section of a thin sample material 776. In this embodiment, the employed radio-nuclide 730 need only produce two coincident gamma rays. The Compton imager computes Compton direction cones 772, 774 for the two coincident gamma rays, respectively. A three-dimensional nuclide location 794 is determined by the intersection of conical surfaces 782, 784 of two Compton direction cones 772, 774 and the thin sample material 776. The location 794 will typically be limited to a single position as depicted in FIG. 7 or perhaps two positions.

In an additional, further alternative embodiment, the radio-nuclide emits four or more simultaneous gamma rays during a single nuclear decay event. In this case, there is an increased probability for the detection of three gamma rays, thereby providing improved images with a lower radiation dose. This alternative could be realized, for example, with the detection of the 424 keV gamma and/or 511 keV gamma rays; that are associated with $^{94}$Tc with low branching ratios, or with imaging of radio-nuclides formed by neutron capture followed by a gamma ray cascade.

In a further alternative embodiment, the various Compton imagers may include a coded aperture placed between patient and the first detector array. The size of open pixels in the coded aperture are selected to be ⅓ to ½ the position resolution of detectors forming the first detector array. This combination results in improved imaging resolution of the radioactive source at the expense of detection efficiency.

The Compton devices described herein can be reduced in size and adapted to image a small volume. As a result, a detector configuration size is substantially reduced from that required for medical imaging of human patients. This configuration is applicable to small animal (e.g. mice) imaging that is widely utilized in the pharmaceutical industry for testing the efficacy of drugs. It is evident that the image resolution will be improved in this embodiment where the distance from the radio-nuclide source to the first interaction sites are minimized The various Compton devices can be adapted for use for the detection of trace constituents of radioactivity in matter. This approach is very sensitive due to the exceptionally low background resulting from the coincident requirement and the high efficiency that can be achieved. A potential application would be the detection of trace amounts by neutron activation of a sample, and the detection of selected radio-nuclides that are identified by their coincident gamma ray emission. Neutron capture usually results in a cascade of several gamma rays from an excited state with a total energy of 7–8 MeV.

The Compton devices can be used for numerous imaging purposes to achieve three-dimensional images. As a medical imager, all locations of radio-nuclide decay are summed together over a predetermined time interval to determine the volumetric image of the location of the radio-pharmaceutical. This approach is applicable to the search for tumors that have an affinity for the selected radio-pharmaceutical.

Figure 5B:
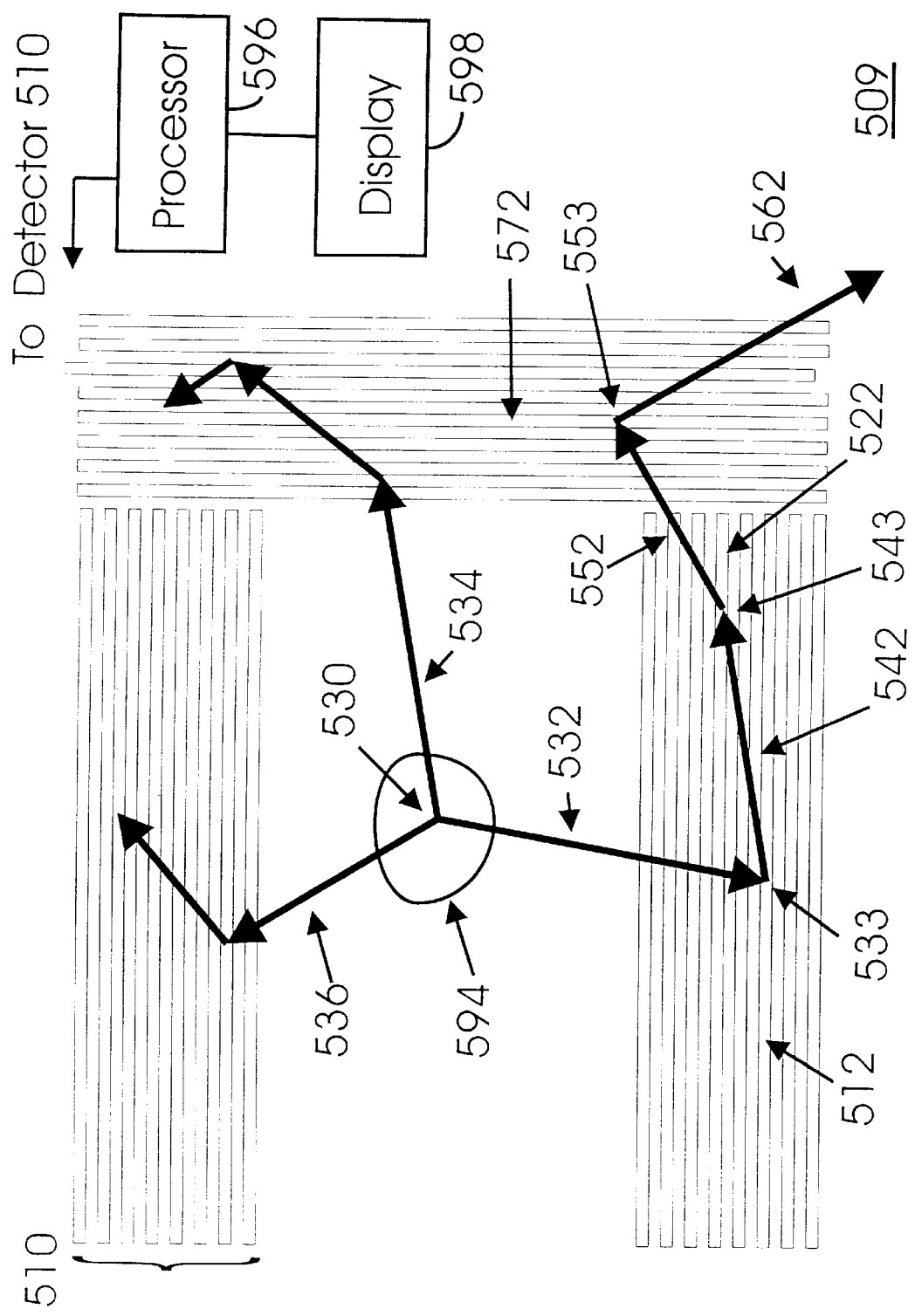
FIG. 5(b) is a cross sectional view of a Compton imager comprising a plurality of detector arrays for detecting coincident Compton scattering of three gamma rays, one of which is the gamma ray of FIG. 5(a)

When the Compton imagers are used to study organ tissue and functions, the detector configuration is adapted to provide optimal coincident imaging for selected organs. The detector configurations shown in FIGS. 1, 5(b) and 6(a) are illustrative only. Alternative configurations can be designed to achieve optimal imaging of various organs, such as the brain, heart, breast, GI tract, etc.

Further, the Compton imagers can be adapted to provide dynamic imaging. As such, all locations of radio-nuclide decay are accumulated over limited time intervals to generate three-dimensional images as a function of time. The time intervals could be sequential or they could be cyclic where the summed images are accumulated in phase, e.g. with heart rate. This approach is applicable to heart perfusion studies or brain function studies.

As will be evident from the foregoing, the Compton imager of the invention provides several important advantages over contemporary nuclear imaging systems. The present Compton imager does not require collimation, and therefore the imager has a much higher efficiency than SPECT techniques that typically use collimators with 0.001–0.01% transmission efficiency. For example, the efficiency for detection of the first gamma ray 32 via Compton scattering in the detector array 10 can be about 25%–30% and the efficiency for detection of the scattered gamma ray in the detector array 20 can be near unity. For Compton scattering in the detector array 10, the maximum efficiency is determined by the requirement that one and only one interaction occurs in the first detector. This results in an optimum thickness for the detector that is about 3–5 cm for silicon detectors and 2–3 cm for germanium detectors. This results in an efficiency of one to 2 percent for a triple coincidence. Thus for each decay event, the present Compton imager determines a point origin as compared to a "line" origin determined by a SPECT technique for each SPECT event.

Further, the present imager provides for improved imaging resolution. Each coincident event can be determined to about 1–2 mm precision. For this, it is assumed that the interaction site is located to about 0.5 mm in both detector array 10 and detector array 20, that these interaction sites 52, 62 in detectors 12, 22, respectively are separated typically by 20 cm, that the angular widths of the Compton cones are +0.5 degree, and that the typical distance from the source to the detector 12 is 10–20 cm. This compares favorably with state-of-the-art PET and SPECT imaging systems. As will be apparent to one of ordinary skill in the art, the size of the source volume also depends on the emission angles between the primary gamma rays. Gamma rays emitted in nearly the same direction will result in extended reconstructed source volumes. These events can be discarded if they contribute excessive image smearing.

In addition, the present imager provides for a lower dose requirement than conventional nuclear imaging techniques. The combination of higher efficiency and much better definition of the possible source volumes compared to SPECT will result in a lower patient dose, e.g. by up to a factor of 100–1000, to achieve similar quality images.

Enhanced imaging of dynamic phenomena is provided through the use of various radio-nuclides employed by the present imager. For example, the present Compton imager can employ $^{94}$Tc-labeled radio-pharmaceuticals which provides for a reduced Compton scattering in a patient that could limit the imaging capability of nuclear medicine systems. The probability for Compton scattering of the $^{94}$Tc gamma rays is about one half that for $^{99m}$Tc, a commonly used nuclide in contemporary SPECT nuclear imaging systems.

Further, the better imaging capability and much higher efficiencies achieved by the present Compton imager when employing $^{94}$Tc means that image acquisition times are reduced by about a factor of 1000 compared to $^{99m}$Tc SPECT. With this dramatic improvement, it will be possible to acquire images on much shorter time scales, enabling dynamic imaging of, e.g. heart function.

The use of high-energy gamma ray lines results in lower Doppler broadening and improved image resolution. As discussed above, enhanced angular image resolution is provided by a lower Doppler broadening.

Although the invention has been described above in relation to preferred embodiments thereof, it will be understood by those skilled in the art that variations and modifications can be effected in these preferred embodiments without departing from the scope and spirit of the invention.

What is claimed is:

1. An imaging device for generating three-dimensional images from a radio-nuclide emitting first, second and third initial gamma rays as simultaneous or nearly simultaneous emissions resulting from a single nuclear decay event, said imaging device comprising:
    a position-sensitive gamma ray detector comprising at least one position sensitive layer, said detector being adapted to determine the locations of interaction sites at which gamma rays undergo one of Compton scatter and photoelectric interactions; and
    a processor for determining a radio-nuclide location as a function of (i) at least two energy values corresponding to each of the first, second and third initial gamma rays,, (ii) detected locations of first interaction sites of the first, second and third initial gamma rays, respectively, and (iii) detected locations of second interactions sites of Compton scattered gamma rays corresponding to the first, second, and third initial gamma rays, respectively,
    the at least two energy values being selected from the group consisting of the energy of a respective initial gamma ray, a first deposition energy of the respective initial gamma ray at the respective first interaction site, energy of said first Compton scattered gamma ray of a respective first initial gamma ray, and a second deposition energy of the corresponding Compton scattered gamma ray at the respective second interaction site, and said processor generating a three-dimensional image by superposition of individual radio-nuclide locations.

2. The device of claim 1, wherein said detector comprises a plurality of position-sensitive silicon detector layers.

3. The device of claim 1, wherein said processor determines a positron-emitting radio-nuclide location as an intersection of a Compton direction cone corresponding to the first initial gamma ray with a line joining a second initial gamma ray first interaction site and a third initial gamma ray first interaction site, said line joining first interaction sites of two 511 keV gamma rays produced in positron-electron annihilation.

4. The device of claim 1, wherein said processor determines the radio-nuclide location as a function of the location of each first interaction site, each second interaction site, and at least two energy values corresponding to each of the three initial gamma rays, said at least two energy values are selected from the group consisting of an initial gamma ray energy of the respective initial gamma rays, a first deposition energy of the respective gamma ray at the respective first interaction site, the energy of the first Compton scattered gamma ray of the respective first initial gamma ray, and a second deposition energy of the respective Compton scattered gamma ray at the respective second interaction site.

5. The device of claim 4, wherein said processor determines radio-nuclide location from a common point of intersection of three Compton direction cones, each Compton direction cone corresponding to one of the three initial gamma rays emitted as a function of a respective scattering angle, the location of the respective first interaction site and the location of the respective second interaction site.

6. A system for generating three-dimensional images, said system comprising:
    a radio-nuclide emitting first, second and third initial gamma rays as simultaneous or nearly simultaneous emissions resulting from a single nuclear decay event;
    a position-sensitive gamma ray detector adapted to determine the locations of multiple interaction sites at which gamma rays undergo one of Compton scatter and photoelectric interactions; and
    a processor for determining a radio-nuclide location as a function of (i) at least two energy values corresponding to each of the first, second and third initial gamma rays, (ii) detected locations of first interaction sites of the first, second and third initial gamma rays, respectively, and (iii) detected locations of second interactions sites of Compton scattered gamma rays corresponding to the first, second, and third initial gamma rays, respectively,
    the at least two energy values being selected from the group consisting of the energy of a respective initial gamma ray, a first deposition energy of the respective initial gamma ray at the respective first interaction site, the energy of the first Compton scattered gamma ray of the respective initial gamma ray, and a second deposition energy of the corresponding Compton scattered gamma ray at the respective second interaction site, said processor generating a three-dimensional image by superposition of individual radio-nuclide locations.

7. The method of claim 6, wherein said position-sensitive detector comprises a plurality of position-sensitive silicon detector layers.

8. The system of claim 6, wherein said radio-nuclide generates three coincident gamma rays during nuclear decay.

9. The system of claim 6, wherein said radio-nuclide generates a positron and said first initial gamma ray during nuclear decay, said positron annihilating with an electron generating said second and said third initial gamma rays.

10. The system of claim 9, wherein said processor determines the location of the radio-nuclide as an intersection of a Compton direction cone corresponding to the first initial gamma ray with a line joining the second initial gamma ray first interaction site and the third initial gamma ray first interaction site.

11. The system of claim 6, wherein said processor determines the location of the radio-nuclide as a function of the location of each first interaction site, each second interaction site, and at least two energy values corresponding to each of the three initial gamma rays, said at least two energy values are selected from the group consisting of the energy of the respective initial gamma ray, a first deposition energy of the respective gamma ray at the respective first interaction site, the energy of the first Compton scattered gamma ray of the respective initial gamma ray, and a second deposition energy of the respective Compton scattered gamma ray at the respective second interaction site.

12. The system of claim 11, wherein said processor determines the location of the radio-nuclide from a common point of intersection of three Compton direction cones, each Compton direction cone corresponding to one of the three initial gamma rays emitted as a function of a respective scattering angle, the location of the respective first interaction site and the location of the respective second interaction site.

13. An imaging device for generating three-dimensional images by detecting initial gamma rays emitted as simultaneous or nearly simultaneous emissions resulting from a single nuclear decay event of a radio-nuclide and three subsequent Compton scattered gamma rays resulting from Compton scattering of the respective initial gamma rays, said imaging device comprising:

a first position-sensitive detector for providing a Compton scattering medium for the initial gamma rays to interact at a respective first interaction site in said first position-sensitive detector and to thereby generate Compton scattered gamma rays, and for detecting a respective location of each first interaction site;

a second position-sensitive detector, surrounding said first position-sensitive detector, for detecting a respective location of a respective second interaction site in said second position-sensitive detector at which the Compton scattered gamma rays interact, said second position-sensitive detector permitting at least a portion of the energy associated with the scattered gamma rays to exit from said second position-sensitive detector; and a processor for determining location of the radio-nuclide as a function of (i) at least two energy values corresponding to each of a first, second and third of the respective initial gamma rays, (ii) the respective locations of each detected first interaction sites, and (iii) the location of the second interaction site where the Compton scattered gamma rays corresponding to the respective initial gamma ray interacts with the second position-sensitive detector, said at least two energy values being selected from the group consisting of an initial gamma ray energy of the first initial gamma ray, a first deposition energy of the respective initial gamma ray at the respective first interaction site, the energy of the first Compton scattered gamma ray of the respective initial gamma ray, and a second deposition energy of a corresponding Compton scattered gamma ray of the first initial gamma ray, at the respective second interaction site, said processor for generating a three-dimensional image by superposition of individual locations of separate radioactive decay positions.

14. The imaging device of claim 13, wherein said first position-sensitive detector is further for detecting energy depositions at respective first interaction sites.

15. The imaging device of claim 13, wherein said second position-sensitive detector is further for detecting energy depositions at respective second interaction sites.

16. The imaging device of claim 13, wherein said first position-sensitive detector is disposed on said second position-sensitive detector to form a multi-layered array.

17. The imaging device of claim 13, wherein said first position-sensitive detector and said second array position-sensitive detection are disposed such that a large solid angle, e.g., greater than three π steradians, is subtended by each said detector relative to a region-of-interest.

18. The imaging device of claim 13, wherein the single nuclear decay event results in three initial gamma rays and said processor determines the location of the radio-nuclide as a function of the (i) locations of each first interaction site, (ii) each second interaction site, and (iii) at least two energy values corresponding to three initial gamma rays, said at least two energy values are selected from the group consisting of the energy of the respective initial gamma rays, a first deposition energy of the respective gamma ray at the respective first interaction site, the energy of the first Compton scattered gamma ray of the respective first initial gamma ray, and a second deposition energy of the respective Compton scattered gamma ray at the respective second interaction site.

19. The imaging device of claim 18, wherein said processor is further for computing a respective scattering angle of the three initial gamma rays at the respective first interaction sites.

20. The imaging device of claim 19, wherein said processor determines the location of the radio-nuclide from a common point of intersection of three Compton direction cones, each cone corresponding to one of the three initial gamma rays emitted as a function of the respective scattering angle, the location of the respective first interaction site and the location of the respective second interaction site.

21. The imaging device of claim 13, wherein said processor determines the location of the radio-nuclide as a common point of an intersection of two Compton direction cones and a thin region-of-interest containing a radioactive substance that emits two coincident gamma rays, the Compton direction cones corresponding to the two coincident gamma rays, respectively, as a function of a respective scattering angle, the location of a respective first interaction site and the location of a respective second interaction site.

22. The imaging device of claim 13, wherein said processor determines the location of a positron-emitting radio-nuclide as an intersection of a Compton direction cone corresponding to the first initial gamma ray with a line joining the first interaction sites corresponding to a second initial gamma ray and a third initial gamma ray of the three initial gamma rays, said second and third initial gamma rays having energies of 511 keV.

23. The imaging device of claim 13, wherein said first position-sensitive detector array provides a three-dimensional position resolution at least one mm and an energy detection resolution of at least 2 keV.

24. The imaging device of claim 13, wherein said second position-sensitive detector provides position resolution of at least one mm.

25. The imaging device of claim 13, wherein said second position-sensitive detector comprises a high-Z detector, said high-Z detector selected to optimize the probability for a photoelectric effect interaction.

26. The imaging device of claim 13, wherein said first position-sensitive detector comprises silicon detectors.

27. The imaging device of claim 13, wherein said second position-sensitive detector comprises one of germanium and/or CdZnTe and/or CdTe and/or GaAs detectors.

28. The imaging device of claim 13, wherein said first position-sensitive detector is further for measuring an energy loss of the gamma rays at a respective first interaction site.

29. The imaging device of claim 13, wherein said second position-sensitive detector is further for measuring an energy loss of the Compton scattered gamma rays at a respective second interaction site.

30. The imaging device of claim 13, further comprising at least a third position-sensitive detector surrounding said second position-sensitive detector, said third position-sensitive detector for providing a gamma ray interaction media for the respective second Compton scattered gamma rays, thereby resulting in generating respective secondary Compton scattered gamma rays, and for detecting a respective location of a respective third interaction site along said third position-sensitive detector where the second Compton scattered gamma rays interact.

31. A method for generating three-dimensional images, said method comprising the steps of:

providing a radio-nuclide source generating three initial gamma rays as simultaneous or nearly simultaneous emissions resulting from a single nuclear decay event;

using a position-sensitive detector to detect locations of three first interaction sites at which the three initial gamma rays respectively interact with the position-sensitive detector;

generating three Compton scattered gamma rays from the three initial gamma rays, respectively, as a result of the three initial gamma rays interacting with the position-sensitive detector;

using the position-sensitive detector to detect locations of three second interaction sites where the three Compton scattered gamma rays interact with the position-sensitive detector, respectively;

determining the location of the radio-nuclide as a function of (i) at least two energy values corresponding to each of the three initial gamma rays, (ii) the location of each detected first interaction site, and (iii) the location of each detected second interaction site, the at least two energy values are selected from the group consisting of the respective energy of the respective initial gamma rays, a first deposition energy of the initial gamma rays at the respective first interaction sites, the energy of the first Compton scattered gamma ray of the respective first initial gamma ray, and a second deposition energy of the Compton scattered gamma rays at the respective second interaction sites; and producing a three-dimensional image by superposition of individual locations of separate radioactive decay positions.

32. The method of claim 31, further comprising the step of measuring energy depositions at each first interaction sites from each of the three initial gamma rays, respectively.

33. The method of claim 31, further comprising the step of measuring energy depositions of each Compton-scattered gamma ray at each respective second interaction sites.

34. The method of claim 31, wherein said determining the location of the radio-nuclide step comprises determining scattering angles for the three initial gamma rays at the respective first interaction sites thereby providing for defining three Compton direction cones, one for each initial gamma ray, an intersection of the three Compton direction cones with each other defining the location of the radio-nuclide.

35. The method of claim 31, further comprising generating images of dynamic phenomena through time sequential acquisition of the three-dimensional images.

36. A method for generating three-dimensional images, said method comprising the steps of:
providing a radio-nuclide source generating nuclear decay as a positron and a first coincident gamma ray, the positron annihilating with an electron to thereby generate a second gamma ray and a third gamma ray;

using a position-sensitive detector to detect locations of first, second, and third gamma ray first interaction sites where the first, second and third gamma rays interact with the position-sensitive detector, respectively;

generating a first Compton scattered gamma ray from the first gamma ray, as a result of the first gamma ray interacting with the first position-sensitive detector;

using the position-sensitive detector to detect a location of a second interaction site where the first Compton scattered gamma ray interacts with the position-sensitive detector;

determining the location of the radio-nuclide as an intersection of a Compton direction gamma ray cone corresponding to the first gamma ray and a line connecting the second and third gamma ray first interaction sites; and producing a three-dimensional image by superposition of individual locations of separate radioactive decay positions.

37. The method of claim 36, wherein the Compton direction cone satisfies a function of at least two energy values corresponding to the first gamma ray, the location of the first gamma ray first interaction, and the location of the second interaction site, the at least two energy values are selected from the group consisting of the energy of the first gamma ray, a first deposition energy of the first gamma ray at the first gamma ray first interaction site, the energy of the first Compton scattered gamma ray of the respective first initial gamma ray, and a second deposition energy of the first Compton scattered gamma ray at the second interaction site.

38. The method of claim 36, further comprising generating images of dynamic phenomena through time sequential acquisition of the three-dimensional images.

39. A method for generating three-dimensional images, said method comprising the steps of:
providing a radio-nuclide source generating nuclear decay as a first coincident gamma ray and a second coincident gamma ray;

administering the radio-nuclide source to a thin region-of-interest;

using a first position-sensitive detector to detect a location of a first gamma ray first interaction site where the first gamma ray interacts with the first position-sensitive detector and a location of a second gamma ray first interaction site where the second gamma ray interacts with the first position-sensitive detector;

generating a first Compton scattered gamma ray and a second Compton scattered gamma ray from the first gamma ray and second gamma ray, respectively, as a result of the first gamma ray and second gamma ray interacting with the first position-sensitive detector, respectively;

using a second position-sensitive detector to detect a first gamma ray second interaction site at which the first Compton scattered gamma ray interacts with the second position-sensitive detector and a second gamma ray second interaction site at which the second Compton scattered gamma ray interacts with the second position-sensitive detector;

determining the location of the radio-nuclide as an intersection of a first Compton direction cone corresponding to the first gamma ray, a second Compton direction cone corresponding to the second gamma ray, and the thin region-of-interest; and producing a three-dimensional image by superposition of individual locations of separate radioactive decay positions.

40. The method of claim 39, wherein each Compton direction cones satisfies a function of at least two energy values corresponding to a respective gamma ray, the location of the respective first interaction site, and the location of the respective second interaction site, the at least two energy values are selected from the group consisting of the energy of the respective initial gamma ray, a first deposition energy of the respective gamma ray at the respective first interaction site, the energy of the first Compton scattered gamma ray of the respective first initial gamma ray, and a second deposition energy of the respective Compton scattered gamma ray at the respective second interaction site.

41. The method of claim 39, further comprising generating images of dynamic phenomena through time sequential acquisition of the three-dimensional images.

42. A system for generating three-dimensional images, said system comprising:
a radio-nuclide emitting a first, second and third initial gamma ray as simultaneous or nearly simultaneous emission resulting from a single nuclear decay event;

a first position-sensitive detector for providing a Compton scattering medium for the first, second and third initial gamma rays to interact, to thereby produce first, second, and third Compton scattered gamma rays, respectively, and for detecting a respective location of each of the first, second and third initial gamma rays at a first, second, and third initial gamma ray first interaction site, respectively, in said first position-sensitive detector;

a second position-sensitive detector surrounding said first position-sensitive for detecting locations of the first, second and third Compton scattered gamma rays at a first, second and third Compton gamma ray second interaction site, respectively, in said second position-sensitive detector, said second position-sensitive detector permitting at least a portion of the energy associated with the scattered gamma rays to exit from said second position-sensitive detector; and a processor for determining a location of the radio-nuclide as a function of (i) at least two energy values corresponding to each of the three initial gamma rays, (ii) the locations of each detected first interaction sites, and (iii) the locations of the first Compton-scattered gamma ray second interaction sites, said at least two energy values are selected from the group consisting of the energy of the first respective gamma ray, a first deposition energy of the respective initial gamma ray at the respective first interaction site, the energy of the respective Compton scattered gamma ray of the respective first initial gamma ray, and a second deposition energy of the respective Compton scattered gamma ray at the respective second interaction site, said processor for generating a three-dimensional image by superposition of individual locations of separate radioactive decay positions.

43. The system of claim 42, wherein said radio-nuclide generates three coincident gamma rays during nuclear decay.

44. The system of claim 42, wherein said radio-nuclide generates a positron and said first initial gamma ray during nuclear decay, said positron annihilating with an electron generating said second and said third initial gamma rays.

45. The system of claim 44, wherein said processor determines the location of a positron-emitting radio-nuclide as an intersection of a Compton direction cone corresponding to the first initial gamma ray with a line joining the second initial gamma ray first interaction site and the third initial gamma ray first interaction site.

46. The system of claim 42, wherein said processor determines the location of the radio nuclide as a function of the location of each first interaction site, each second interaction site, and at least two energy values corresponding to each of the three initial gamma rays, said at least two energy values are selected from the group consisting of the energy of the respective initial gamma ray, a first deposition energy of the respective gamma ray at the respective first interaction site, the energy of the first Compton scattered gamma ray of the respective first initial gamma ray, and a second deposition energy of the respective Compton scattered gamma ray at the respective second interaction site.

47. The system of claim 46, wherein said processor determines the location of the radio-nuclide from a common point of intersection of three Compton direction cones, each Compton direction cone corresponding to one of the three initial gamma rays emitted as a function of a respective scattering angle, the location of the respective first interaction site and the location of the respective second interaction site.

48. The system of claim 42, further comprising at least a third position-sensitive detector surrounding said second position-sensitive detector, said third position-sensitive detector for providing a gamma ray interaction media for the Compton scattered gamma rays, thereby generating secondary Compton scattered gamma rays, respectively, and for detecting locations of the secondary Compton scattered gamma rays at a respective third interaction site in said third position-sensitive detector.

49. The system of claim 42, wherein respective energy losses $L_1$ and $L_2$ at the respective first and second interaction sites of each respective initial gamma ray and scattering angles at said respective second interaction sites are used to determine energies and direction cones of said respective initial gamma rays.

50. A method for generating three-dimensional images, said method comprising the steps of:

providing a radio-nuclide source generating three initial gamma rays as simultaneous or nearly simultaneous emissions resulting from a single nuclear decay event;

detecting locations of three first interaction sites at which the three initial gamma rays, respectively, interact with a single position-sensitive detector;

generating three Compton scattered gamma rays from the three initial gamma rays, respectively, as a result of the three initial gamma rays interacting with the position-sensitive detector;

detecting locations of three second interaction sites where the three Compton scattered gamma rays respectively interact with the positron-sensitive detector;

determining the location of the radio-nuclide as a function of (i) at least two energy values corresponding to each of the three initial gamma rays, (ii) the location of each detected first interaction site, and (iii) the location of each detected second interaction site, the at least two energy values are selected from the group consisting of the energy of the respective initial gamma rays, a first deposition energy of the initial gamma rays at the respective first interaction sites, the energy of the first Compton scattered gamma ray of the respective first initial gamma ray, and a second deposition energy of the Compton scattered gamma rays at the respective second interaction sites; and producing a three-dimensional image by the superposition of individual locations of separate radioactive decay positions.

51. The method of claim 50, further comprising the step of measuring energy depositions at each first interaction site from each of the three initial gamma rays, respectively.

52. The method of claim 50, further comprising the step of measuring energy depositions of each respective Compton-scattered gamma ray at each respective second interaction site.

53. The method of claim 50 wherein said determining the location of the radio-nuclide step comprises determining scattering angles for the three initial gamma rays at the respective first interaction sites thereby providing for defining three Compton direction cones, one for each initial gamma ray, an intersection of the three Compton direction cones with each other defining the location of the radio-nuclide.

54. The method of claim 50, further comprising generating images of dynamic phenomena through time sequential acquisition of the three-dimensional images.

55. The method of claim 50, wherein the position-sensitive detector comprises a plurality of position-sensitive silicon detector layers.

56. A method for generating three-dimensional images, said method comprising the steps of:

providing a radio-nuclide source generating nuclear decay as a positron and a first coincident gamma ray, the positron annihilating with an electron to thereby generate a second gamma ray and a third gamma ray;

detecting locations of a first, second, and third gamma ray first interaction sites where the first, second and third gamma rays interact with a single position-sensitive detector, respectively;

generating a first Compton scattered gamma ray from the first gamma ray, as a result of the first gamma ray interacting with the position-sensitive detector;

detecting a location of a second interaction site where the first Compton scattered gamma ray interacts with the position-sensitive detector;

determining the location of the radio-nuclide as an intersection of a Compton direction gamma ray cone corresponding to the first gamma ray and a line connecting the second and third gamma ray first interaction sites, said second and third initial gamma rays having energies of 511 keV; and producing a three-dimensional image by superposition of individual locations of separate radioactive decay positions.

57. The method of claim 56, further comprising the step of measuring energy depositions at each first interaction sites from each of the three initial gamma rays, respectively.

58. The method of claim 56, wherein the Compton direction cone satisfies a function of at least two energy values corresponding to the first gamma ray, the location of the first gamma ray first interaction, and the location of the second interaction site, the at least two energy values are selected from the group consisting of the energy of the first gamma ray, the deposition energy of the first gamma ray at the first gamma ray first interaction site, the energy of the first Compton-scattered gamma ray of the respective first initial gamma ray, and a second deposition energy of the first Compton scattered gamma ray at the second interaction site.

59. The method of claim 56, further comprising generating images of dynamic phenomena through time sequential acquisition of the three-dimensional images.

* * * * *

UNITED STATES PATENT AND TRADEMARK OFFICE
CERTIFICATE OF CORRECTION

PATENT NO. : 6,484,051 B1  Page 1 of 1
DATED : November 19, 2002
INVENTOR(S) : Kurfess, James Daniel It is certified that error appears in the above-identified patent and that said Letters Patent is hereby corrected as shown below:

<u>Title page,</u>
Item [76], should read:

-- [76]  Inventor:  James Daniel Kurfess, 1708 Justin Dr., Gambrills, MD (US) 21054 --

Signed and Sealed this

Eighth Day of April, 2003

JAMES E. ROGAN
*Director of the United States Patent and Trademark Office*